(12) United States Patent
Adler

(10) Patent No.: US 9,291,578 B2
(45) Date of Patent: Mar. 22, 2016

(54) X-RAY PHOTOEMISSION MICROSCOPE FOR INTEGRATED DEVICES

(76) Inventor: David L. Adler, San Jose, CA (US)

( * ) Notice: Subject to any disclaimer, the term of this patent is extended or adjusted under 35 U.S.C. 154(b) by 680 days.

(21) Appl. No.: 13/507,895

(22) Filed: Aug. 3, 2012

(65) Prior Publication Data

US 2014/0037052 A1   Feb. 6, 2014

(51) Int. Cl.
  *G21K 7/00*    (2006.01)
  *G01N 23/04*   (2006.01)

(52) U.S. Cl.
  CPC ........ *G01N 23/04* (2013.01); *G01N 2223/1006* (2013.01); *G01N 2223/611* (2013.01); *G21K 7/00* (2013.01)

(58) Field of Classification Search
  CPC ....... G21K 7/00; G21K 1/06; G21K 2201/64; G01N 23/04; G01N 23/18; G01N 23/043
  USPC ..................................................... 378/43, 140
  See application file for complete search history.

(56) References Cited

U.S. PATENT DOCUMENTS

| | | | |
|---|---|---|---|
| 1,203,495 A | 10/1916 | Coolidge | |
| 1,211,092 A | 1/1917 | Coolidge | |
| 1,215,116 A | 2/1917 | Coolidge | |
| 1,328,495 A | 1/1920 | Coolidge | |
| 1,355,126 A | 10/1920 | Coolidge | |
| 2,617,942 A | 11/1952 | McLachlan, Jr. et al. | |
| 2,814,729 A | 11/1957 | Newberry et al. | |
| 2,877,353 A | 3/1959 | Newberry | |
| 3,778,614 A | 12/1973 | Hounsfield | |
| 3,973,127 A | 8/1976 | Matsuda et al. | |
| 4,115,698 A | 9/1978 | Hounsfield | |
| 4,144,457 A | 3/1979 | Albert | |
| 4,317,036 A | 2/1982 | Wang | |
| 4,870,674 A | 9/1989 | Schmahl et al. | |
| 5,045,696 A | 9/1991 | Hirose | |
| 5,222,113 A | 6/1993 | Thieme et al. | |
| 5,276,724 A | 1/1994 | Kumasaka et al. | |
| 5,434,901 A | 7/1995 | Nagai et al. | |
| 5,550,887 A | 8/1996 | Schmal et al. | |
| 6,002,740 A * | 12/1999 | Cerrina et al. | 378/43 |

(Continued)

OTHER PUBLICATIONS

W.C. Röntgen, Ueber eine neue Art von Strahlen (Würzburg Verlag, Würzburg, Germany, 1895) also, in English, "On a New Kind of Rays," Nature, vol. 53, pp. 274-276 (Jan. 23, 1896).

(Continued)

*Primary Examiner* — Courtney Thomas
(74) *Attorney, Agent, or Firm* — Franklin Schellenberg

(57) ABSTRACT

An apparatus is disclosed for the examination and inspection of integrated devices such as integrated circuits. X-rays are transmitted through the integrated device, and are incident on a photoemissive structure that absorbs x-rays and emits electrons. The electrons emitted by the photoemissive structure are shaped by an electron optical system to form a magnified image of the emitted electrons on a detector. This magnified image is then recorded and processed. In some embodiments, the integrated device and photoemissive structure are independently mounted and controlled. In other embodiments, the photoemissive device is deposited directly onto the integrated device. In some embodiments, the incidence angle of the x-rays is varied to allow internal three-dimensional structures of the integrated device to be determined. In other embodiments, the recorded image is compared with a reference data to enable inspection for manufacturing quality control.

38 Claims, 14 Drawing Sheets

(56) References Cited

U.S. PATENT DOCUMENTS

| | | | |
|---|---|---|---|
| 6,526,121 | B1 | 2/2003 | Hwu et al. |
| 7,057,187 | B1 | 6/2006 | Yun et al. |
| 7,095,037 | B2 * | 8/2006 | Fernadez et al. ......... 250/492.24 |
| 7,119,953 | B2 | 10/2006 | Yun et al. |
| 7,215,736 | B1 | 5/2007 | Wang et al. |
| 7,297,959 | B2 | 11/2007 | Yun et al. |
| 7,388,942 | B2 | 6/2008 | Wang et al. |
| 7,394,890 | B1 | 7/2008 | Wang et al. |
| 7,529,338 | B2 * | 5/2009 | Fung .................... G01N 23/043 378/208 |
| 7,561,662 | B2 | 7/2009 | Wang et al. |
| 7,800,072 | B2 | 9/2010 | Yun et al. |
| 7,813,475 | B1 | 10/2010 | Wu et al. |
| 8,139,846 | B2 | 3/2012 | Bajura et al. |
| 2003/0142789 | A1 * | 7/2003 | Harding et al. ............... 378/119 |
| 2004/0005026 | A1 * | 1/2004 | Fujii et al. ....................... 378/43 |
| 2008/0061234 | A1 | 3/2008 | Nakamura |
| 2012/0269323 | A1 | 10/2012 | Adler et al. |
| 2012/0269324 | A1 | 10/2012 | Adler |
| 2012/0269325 | A1 | 10/2012 | Adler et al. |
| 2012/0269326 | A1 | 10/2012 | Adler et al. |

OTHER PUBLICATIONS

Janos Kirz, "Phase zone plates for x rays and the extreme uv", J. Opt. Soc. Am. vol. 64(3), pp. 301-309 (Mar. 1974).

M. Kotera, K. Murata & K. Nagami "Monte Carlo simulation of 1-10-KeV electron scattering in a gold target", J. Appl. Phys. vol. 52(2), pp. 997-1003 (Feb. 1981).

B.L. Henke, J.P. Knauer & K. Premaratne, "The characterization of x-ray photocathodes in the 0.1-10-keV photon energy region", J. Appl. Phys. 52(3), pp. 1509-1520 (Mar. 1981).

G. Schmahl et al., "Zone Plates for X-Ray Microscopy", pp. 63-74 of "X-Ray Microscopy", G. Schmahl & D. Rudolph, eds. (Springer Verlag, Berlin, 1984).

D. Rudolph et al., "The Göttingen X-Ray Microscope and X-Ray Microscopy Experiments at the BESSY Storage Ring", pp. 192-202 of "X-Ray Microscopy", G. Schmahl & D. Rudolph, eds. (Springer Verlag, Berlin, 1984).

O. H. Griffith & W. Engel, "Historical perspective and current trends in emission microscopy, mirror electron microscopy and low-energy electron microscopy," Ultramicroscopy vol. 36, pp. 1-28 (1991).

A.D. Dubner et al., "Diffraction effects in x-ray proximity printing," J. Vac. Sci. Technol. B, vol. 10(5), pp. 2234-2242 (Sep./Oct. 1992).

Henry I. Smith and M.L. Schattenberg, "X-ray lithography from 500 to 30 nm: X-ray nanolithography," IBM J. Res. Develop. vol. 37(3), p. 319-329 (May 1993).

R.N. Watts et al., "A transmission x-ray microscope based on secondary-electron imaging," Rev. Sci. Instrum., vol. 68(9), pp. 3464-3476 (Sep. 1997).

L. Reimer, "Electron Optics of a Scanning Electron Microscope", Ch. 2 (pp. 13-56) of "Scanning Electron Microscopy: Physics of Image Formation and Microanalysis, 2nd Edition", (Springer Verlag, Heidelberg, 1998).

Gelsomina De Stasio et al., "Soft-x-ray transmission photoelectron spectromicroscopy with the MEPHISTO system", Rev. Sci. Instrum. vol. 69(9), pp. 3106-3108 (Sep. 1998).

Gelsomina De Stasio et al., "MEPHISTO spectromicroscope reaches 20 nm lateral resolution", Rev. Sci. Instrum. vol. 70(3), pp. 1740-1742 (Mar. 1999).

Y. Hwu et al., "Using photoelectron microscopy with hard-X-rays", Surface Science vol. 480, pp. 188-195 (2001).

J. Kirz & D. Attwood, "Zone Plates", Sec. 4.4 of the "X-ray Data Booklet", A.C. Thompson & D. Vaughan, eds., Lawrence Berkeley National Laboratory, Berkeley, CA, (Second Edition Jan. 2001); available at < http://xdb.lbl.gov/Section4/Sec_4-4.html >.

Akira Hirakimoto, "*Microfocus X-ray Computed Tomography and Its Industrial Applications*", Analytical Sciences vol. 17 Supplement, pp. i123-i125 (2001).

Akihisa Takeuchi et al., "Submicrometer-resolution three-dimensional imaging with hard x-ray imaging microtomography", Rev. Sci. Instrum. vol. 73(12), pp. 4246-4249 (Dec. 2002).

S. Günther et al., "Photoelectron microscopy and applications in surface and materials science", Progress in Surface Science vol. 70, pp. 187-260 (2002).

"X-Ray Lithography towards 15 nm", Jefferson Lab Technical Note 03-016 Thomas Jefferson National Accelerator Facility, Newport News, Virginia (Jan. 2003).

Yigal Lilach & Micha Asscher, "Steric Effect in Electron-Molecule Interaction", J. Phys. Chem. B vol. 108, pp. 4358-4361 (2004).

Y. Hwu, J.H. Je & G. Margaritondo, "Real-time radiology in the microscale", Nuclear Instruments and Methods in Physics Research A vol. 551, pp. 108-118 (2005).

L.A. Bakaleynikov et al., "Combined X-ray-electron Imaging Techniques: Limitations on Lateral Resolution", Journal of Electron Spectroscopy and Related Phenomena vol. 151, pp. 97-104 (2005).

Thierry Martin & Andreas Koch, "Recent developments in X-ray imaging with micrometer spatial resolution", Journal of Synchrotron Radiation vol. 13, pp. 180-194 (2006).

S.H. Lau et al. "Non destructive characterization of advanced package and die level defects—with novel 3D x-ray micro and nanotomography systems", SEMI's Semiconductor Manufacturing Magazine pp. 1-10 (Feb. 2007).

J.M. Vaughn, K.D. Jamison and M.E. Kordesch, "In Situ Emission Microscopy of Scandium/Scandium—Oxide and Barium/Barium—Oxide Thin Films on Tungsten", IEEE Trans. Electron Devices vol. 56(5), pp. 794-798 (May 2009).

A. Gaur, B.D. Shrivastava & S.K. Joshi, "Copper K-edge XANES of Cu(I) and Cu(II) oxide mixtures", Journal of Physics: Conference Series vol. 190, 012084 (2009).

S.J. Liew, A.A. Malcolm, X.M. Yin, & C.S. Chong, "User-friendly visualisation of industrial X-ray computed tomography", SIMTech Technical Reports vol. 11, No. 2, pp. 92-98 (Apr.-Jun. 2010).

* cited by examiner

X-RAY PHOTOEMISSION MICROSCOPE FOR INTEGRATED DEVICES

FIELD OF THE INVENTION

This invention relates to the examination of integrated devices, such as integrated circuits, by transmitting x-rays through the device and magnifying the resulting images; and in particular, to the use of a hybrid system which converts the transmitted x-rays to electron-beams, which are then magnified using electron optics for the resolution of physical structures much smaller than 100 nm in size. The particular embodiments disclosed here allow for the observation of the device at multiple angles to determine the two-dimensional and three-dimensional structures within the device without physically damaging the device, and, when paired with a reference image or a reference database, can also be used as an inspection system for devices of unknown quality.

BACKGROUND OF THE INVENTION

The initial discovery of x-rays by Röntgen in 1895 [W. C. Röntgen, "Eine Neue Art von Strahlen (Würzburg: Verlag und Druck der Stahel'schen K. Hof-und Universitäts-Buch-und Kunsthandlung, Würzburg, Germany, 1896); "On a New Kind of Rays," Nature, Vol. 53, pp. 274-276 (Jan. 23 1896)] was in the form of shadowgraphs, in which the contrast of x-ray transmission for biological samples (e.g. bones vs. tissue) allowed internal structures to be revealed without damaging the samples themselves. However, because of their short wavelength (10 to 0.01 nm, corresponding to energies in the range of 100-100,000 eV), and the absence of materials for which the refractive index for x-rays differs significantly from 1, there are no easy equivalents to refractive or reflective optical elements so commonly used in optical system design. So, even now, the most common use of x-rays is still as a simple shadowgraph, observing the structure of bones and teeth in the offices of doctors and dentists.

Early x-ray "microscopy," developed more than 50 years after the initial discovery of x-rays, simply consisted of elaborate shadowgraph apparatus, in which the diverging x-rays cast a shadow larger than the object [S. P. Newberry and S. E. Summers, U.S. Pat. No. 2,814,729]. With the advent of computer data collection, it became possible to gather more information from the specimen, changing the relative positions and illumination angles of the x-ray source and specimen in a systematic way. Using multiple transmission measurements taken at multiple angles around the specimen, images can be synthesized by computer that represent a 2-dimensional or 3-dimensional model of the specimen [G. N. Hounsfield, U.S. Pat. No. 3,778,614]. The "slices" of interior bodies so revealed are amazing to look at, revealing a great deal about the internal structures without invasive surgery. However, as far as the physics of the x-ray interaction with the specimen, these tomographic reconstructions represent nothing more than an elaborate map of x-ray absorption—a sophisticated shadowgraph.

Over time, other imaging tools for x-ray optical systems were invented. Apparatus using grazing incidence reflection off of surfaces provided cone reflectors [C. G. Wang, U.S. Pat. No. 4,317,036] and capillary collimators [F. Kumasaka et al., U.S. Pat. No. 5,276,724] to allow a diverging x-ray beam to be manipulated into a collimated beam or to concentrate x-rays onto a specimen.

With the development of high-resolution patterning with electron-beam lithography in the 1970's, Fresnel zone plates, which use diffractive properties to effectively focus an electromagnetic wave, could now be manufactured at the small dimensions suitable for use with short x-ray wavelengths. [J. Kirz, "Phase zone plates for x rays and the extreme uv", Journal of the Optical Society of America, Vol. 64(3), pp. 301-309 (March 1974)]. Zone plates can be used both to shape and focus the illuminating optics and also to collect and focus the transmitted x-rays onto a detector [G. Schmahl and D. Rudolph, "X-Ray Microscopy" pp. 192-202, (Springer Verlag, Berlin, 1984); and U.S. Pat. No. 4,870,674]. Variations using phase-contrast rings [G. Schmal [sic] and D. Rudolph, U.S. Pat. No. 5,550,887] have been developed, and are now commonly used in contemporary x-ray microscopes.

Unfortunately, what a zone plate microscope design may have in resolution may not be matched in imaging speed. The diffractive properties of the zone plate are tuned to a specific wavelength, meaning that most of the energy in a broad-band x-ray source is discarded. Synchrotron sources may increase brightness for a particular wavelength, but are not suitable for portable systems and, at the selected wavelength, the best diffraction efficiency that can be achieved is still under 35%.

Because of this, the microscopy of specimens requiring high speed and high resolution use electron microscopy instead, either as scanning electron microscopes (SEMs) or transmission electron microscopes (TEMs). Being charged particles, electrons can be easily controlled and focused using electric and magnetic fields, and the science and technology of electron optics is a well-developed and established field. [L. Reimer, "Electron Optics", Section 2 of Ch. 2 of "Scanning Electron Microscopy: Physics of Image Formation and Microanalysis, $2^{nd}$ Edition", (Springer Verlag, Heidelberg, 1998)].

Electron beams require that the sample and the beam path must all be in a vacuum. Since any sample would lose all its water in the desiccating environment of a vacuum chamber, this does not represent a way of observing most biological samples in their "natural" condition. Also, depending on their energy, electrons tend to be absorbed with the first few nanometers of a sample, making them extremely useful for the observation of surfaces, but not so useful for the observation of internal structures. Samples must be thinned to be less than 100 nm thick, and often only a few tens of nm thick, before they can be used in a TEM.

In an attempt to combine the penetrating power of x-rays with the control and resolution possible with electron-beams, a hybrid of x-ray microscopy and photoemissive electron microscopy, or PEEM, has been developed [O. H. Griffith and W. Engel, "Historical perspective and current trends in emission microscopy, mirror electron microscopy and low-energy electron microscopy," Ultramicroscopy, Vol. 36, p. 1 (1991)]. Although PEEM is usually a technique in which a surface is excited from the front and photoelectrons also emitted from the same front surface, a photocathode mounted on a sufficiently thin membrane can allow excitation from the back side through a membrane [H. Hirose, U.S. Pat. No. 5,045,696].

FIG. 1 illustrates a prior art hybrid x-ray/PEEM system as disclosed by F. Cerrina and T. B. Lucatorto on Drawing Sheet 2 of U.S. Pat. No. 6,002,740. In this system, described as being a system to inspect masks for x-ray lithography, the mask 22 is placed between a source of x-rays 30 and converter 18 comprising a photo-emitting cathode 16 mounted on a membrane 19. When the converter 18 is illuminated through the membrane 19 by x-rays, it emits electrons 32 whose intensity is "directly proportional to the local intensity of the x-rays impinging thereon."

The electrons 32 emitted from the converter 18 are then highly magnified by a set of electron optics in the electron microscope 17. The electron microscope 17 forms an image of the mask pattern that may be fed to the computer system 20 for analysis and display.

The Cerrina disclosure describes a hybrid x-ray/PEEM inspection system for x-ray lithography masks, in which the system emulates an x-ray lithography system. [H. Smith and M. Schattenberg, "X-ray lithography from 500 to 30 nm," IBM Journal of Research and Development, Vol. 37(3), p. 319 (1993)]. The configuration described requires placing the photoemitting cathode relative to the mask in the same position that a photoresist-coated wafer would be placed in an x-ray lithography system, allowing the image to mimic what the mask would print. In such a lithography system, both the mask and the wafer are placed in a vacuum in close proximity for proximity printing, with a distance of less than 25 microns separating them to minimize distortions, [A. D. Dubner et al., "Diffraction effects in x-ray proximity printing," Journal of Vacuum Science and Technology B, Vol. 10(5), pp. 2234-2242 (1992)] but not in direct contact to avoid damaging the mask or wafer.

Such hybrid systems were proposed but never applied to x-ray lithographic mask inspection because x-ray lithography did not achieve any widespread commercial adoption. Such systems have been built and demonstrated for various biological and mineral samples. [R. N. Watts et al., "A transmission x-ray microscope based on secondary-electron imaging," Review of Scientific Instruments, Vol. 68, p 3464 (1997); G. De Stasio et al., "Soft-x-ray transmission photoelectron spectromicroscopy with the MEPHISTO system," Review of Scientific Instruments, Vol. 69, p. 3106 (1998), and "MEPHISTO spectromicroscope reaches 20 nm lateral resolution," Review of Scientific Instruments, Vol. 70, p. 1740 (1999); Y. Hwu et al., "Using photoelectron microscopy with hard x-rays," Surface Science, Vol. 480, pp. 188-195 (2001)]. However, many biological structures are well observed by variations of conventional optical and x-ray tomographic tools, making the complexity of these hybrid systems unnecessary for many biological applications.

But, for one particular class of specimens, variations on this hybrid technique may be perfectly suited, and are the subject of the invention disclosed here.

One problem that has recently emerged is the need to examine products containing integrated devices, such as integrated circuits (ICs), to verify that the devices have been manufactured as specified. This is especially important when the security and integrity of the devices may be an issue, in which is it necessary to insure that additional circuitry (e.g. RF antennas to relay signals from unauthorized sources) have not been inserted during the manufacturing process. When all circuit structures are encased within a single package, verification of the actual contents of the circuit is difficult.

Current examination techniques for these circuit packages require destructive testing, taking the circuit package and removing material layer by layer, photographing and analyzing the circuit patterns of each layer as they are exposed with either an optical microscope, or with an electron microscope for smaller structures. This can be very tedious and time consuming. With the components of the most modern ICs quickly approaching 20 nm in size, and potentially becoming as small as 5 nm in future generations, there is a real need for an imaging technique which has the resolution to identify these small features and also the speed to observe multiple layers of devices and interconnects over a 1 cm by 1 cm area in a manageable amount of time.

An approach using the transmissive power of x-rays to examine the internal contents of a circuit will not require the destruction of the circuit itself, and has the potential to provide both the resolution needed and the speed required.

Systems using an x-ray microscope for the inspection of integrated circuits have been disclosed by the Xradia Corporation [W. Yun and Y. Wang, U.S. Pat. No. 7,119,953; Y. Wang et al., U.S. Pat. No. 7,394,890; M. Bajura et al., U.S. Pat. No. 8,139,846; <http://www.xradia.com/>]. FIG. 2 illustrates a prior art x-ray microscope system as disclosed on Drawing Sheet 2 of U.S. Pat. No. 7,119,953. In such a system, x-rays from a source 1110 are collected by a condenser 1120, which relays x-rays from the source 1110 to the test object 1010. This condenser 1120 is described in some embodiments as a capillary condenser with a suitably configured reflecting surface, while in others as a zone plate. The converging beam from the condenser 1120 irradiates the test object 1010, and the radiation emerging from the test object 1010 is scattered and diffracted out of the path of the direct radiation beam. An objective 1118 is therefore used to form an image of the object, collecting the scattered x-rays. This objective 1118 is described as being possibly a zone plate lens, a Wolter optic, or a Fresnel optic. In some embodiments, an additional phase plate 1116, often in the form of a ring around the center axis of the system, is included to enhance contrast. Both the phase plate 1116 and the objective 1118 are described as being attached to a "high-transmissive substrate" 1140 to form a composite optic 1138. The image of the test object 1010 is formed on a detector 1125, which is described as possibly comprising in some embodiments a charged coupled device (CCD), and in some embodiments comprising a scintillator, and in others being a film-based detector.

X-ray systems with Fresnel zone plate (FZP) optics such as this prior art Xradia system can be effective for the non-destructive examination of integrated circuits, but the limitations of the zone plate optics [J. Kirz and D. Attwood, "Zone Plates", Sec. 4.4 of the "X-ray Data Booklet" <http://xdb.lbl.gov/Section4/Sec_4-4.html>] reduce the wavelength range over which x-rays can be effectively collected, and increase the time to collect data for a complete IC. The system is therefore very slow and inefficient for collecting large volumes of data on multiple layers of an IC.

There is therefore a need for a system that can combine the penetrating power of x-rays with the easy control possible in electron imaging, and in particular for the application to the microscopy of sub-100 nm structures in integrated circuits to allow rapid, non-destructive testing and inspection of those integrated circuits.

BRIEF SUMMARY OF THE INVENTION

The invention disclosed with this application is an apparatus for the examination and inspection of an integrated device such as an integrated circuit. In this invention, a photoemissive structure placed in a vacuum chamber converts incident x-rays, which have been transmitted through the integrated device, into the emission of electrons, and the electrons emitted by the converter are shaped by an electron optical system to form a magnified image of the emitted electrons on a detector.

In preferred embodiments of the invention, the x-ray intensity pattern incident on the photoemissive structure will have a profile representing the attenuation of x-rays in the integrated device under examination, and the materials of the photoemissive structure will be selected so that the number of electrons emitted are proportional to the intensity of the incident x-rays.

The magnified image produced by the detector can then be recorded and processed. In some embodiments, the image is compared with a corresponding image of a device known to be correct. In another embodiment, the image is compared to a database representation of the structures in the circuit.

In yet another embodiment, the integrated device under examination is mounted on a stage and the incident x-rays are moved through a series of angles and positions relative to the integrated device, and a set of corresponding transmission images recorded. These images can then be assembled using computed laminography algorithms with a digital computer to create a 2-D or 3-D representation of the specimen. This synthesized representation can then be compared to a reference image or database, allowing the embodiment to be used as an inspection system.

In some embodiments of the invention, the integrated device under examination is mounted outside the vacuum chamber containing the photoemissive structure and the electron optics.

In other embodiments of the invention, the photoemissive structure is coated directly onto the window of the vacuum system that contains the electron optics, reducing the distance between the specimen and the photoemissive structure.

In other embodiments of the invention, the specimen to be examined is directly coated with the photoemissive layer, and mounted within the vacuum system containing the electron optics, and is illuminated by x-rays through a suitably transparent window in the wall of the vacuum chamber.

Figure 1:
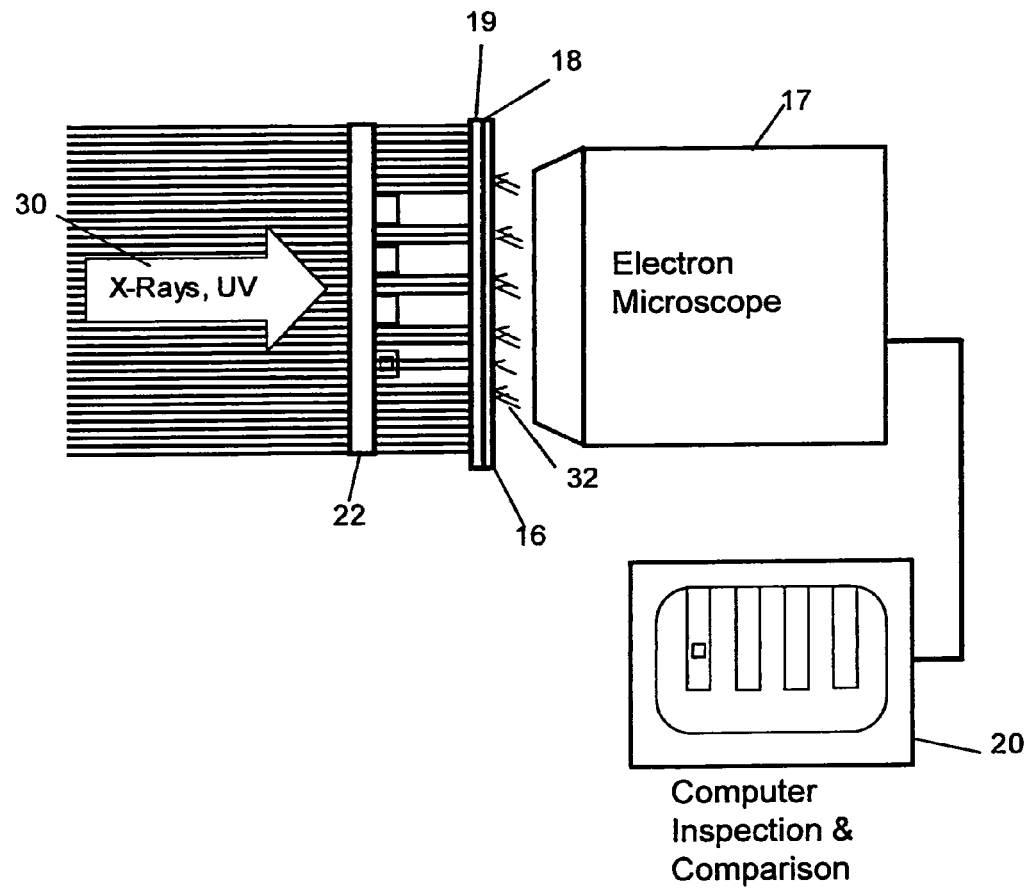
FIG. 1 illustrates a prior art hybrid x-ray/PEEM system as disclosed in U.S. Pat. No. 6,002,740.
Figure 2:
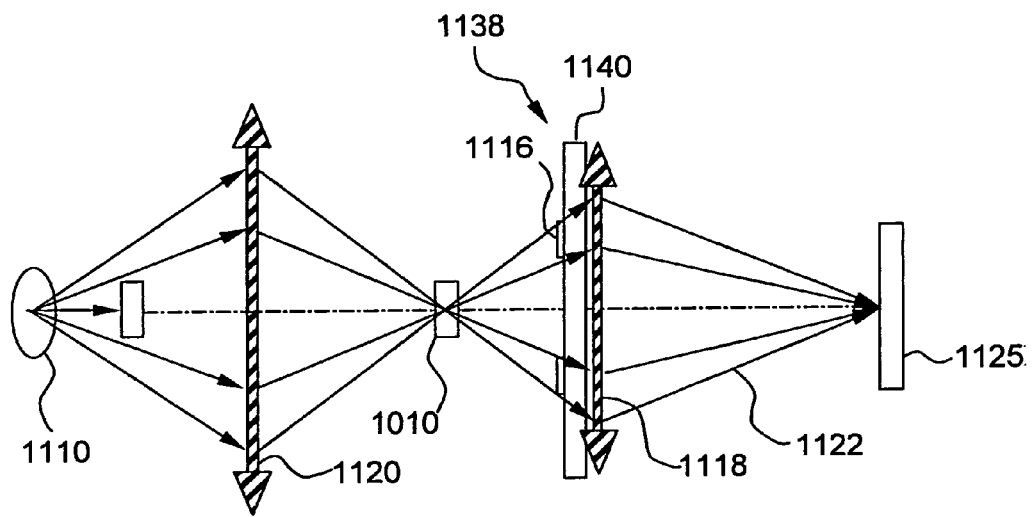
FIG. 2 illustrates a prior art x-ray microscope system from the Xradia Corporation as disclosed in U.S. Pat. No. 7,119, 953.

Note: The elements in the drawings illustrate the elements of the invention and their general relationships, but should not be interpreted as scale drawings. For example, in FIG. 3, the entrance window 125 in the vacuum chamber 120 may be only a few mm in diameter or smaller, while the entire vacuum chamber 120 may be as long as a meter, but these elements have not been shown at these relative dimensions here. Likewise, in FIG. 4, in an integrated device 160, the silicon substrate 162 may be 500 microns thick, whereas the layer comprising integrated structures 164 may be only 10-20 microns thick. The illustrations do show the general relationships sufficiently so that one skilled in the art would be able to reproduce the invention accordingly.

Note: The cross-section views have been selected to represent elements in a plane in which the x-rays and emitted electrons are traveling. Some of the elements also presented in the cross-section views, and in particular the stage controls 132 and 332 inside the vacuum chamber 120 as well as the external stage controls 232 would typically be, at least in part, below or above the plane of the illustrated cross-section, especially for the region through which the x-rays or emitted electrons are traveling, so that these mechanical elements will not block the x-rays. However, the illustrations and descriptions in the specification present the general relationships sufficiently so that one skilled in the art would be able to reproduce the invention accordingly.

DETAILED DESCRIPTIONS OF EMBODIMENTS OF THE INVENTION

First Embodiment of the Invention

Figure 3:
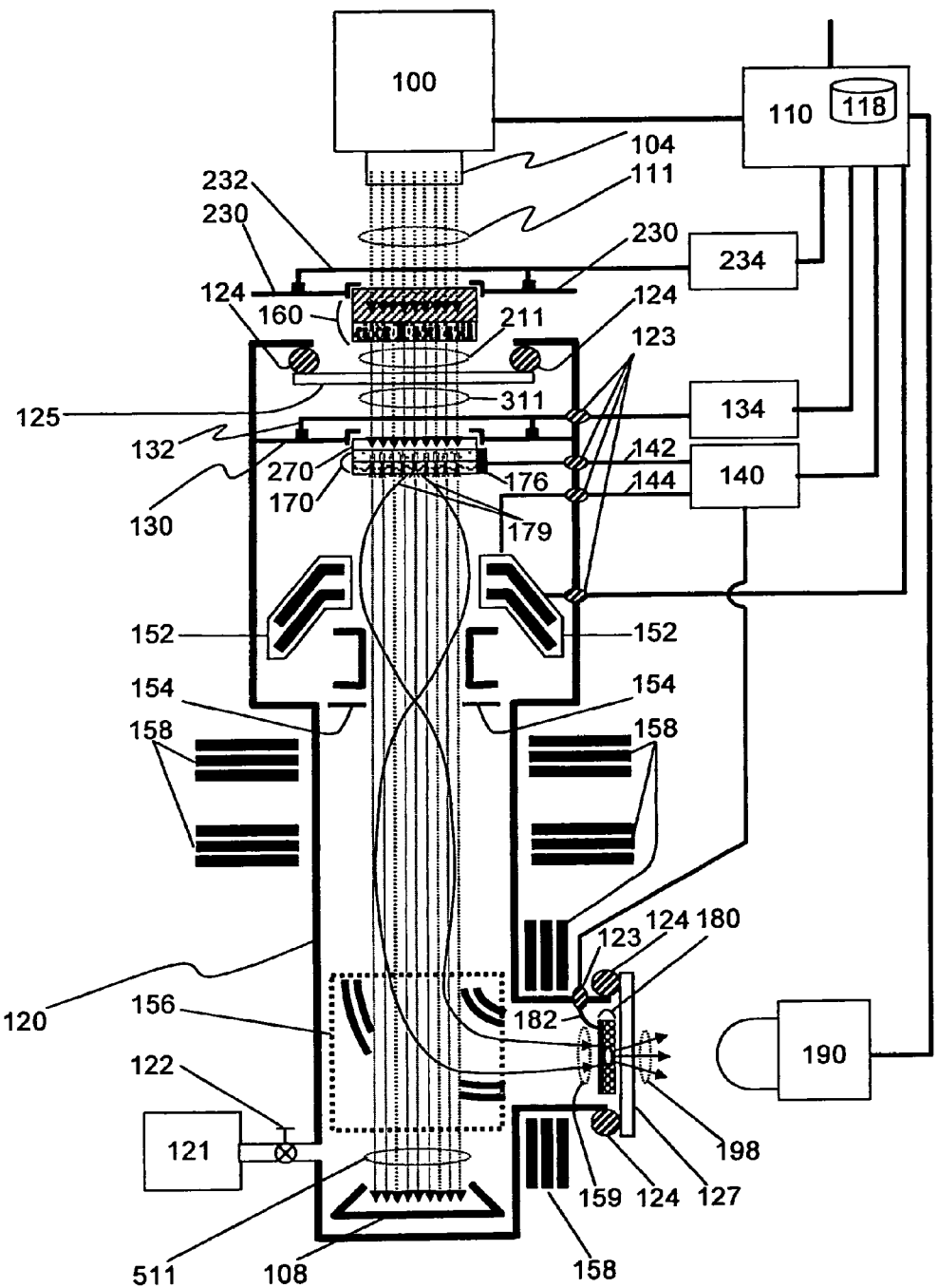
FIG. 3 illustrates a cross-section view of a microscope system according to one embodiment of the present invention, in which the integrated device is mounted outside the vacuum chamber and the photoemissive structure is mounted within the vacuum chamber.
Figure 4:
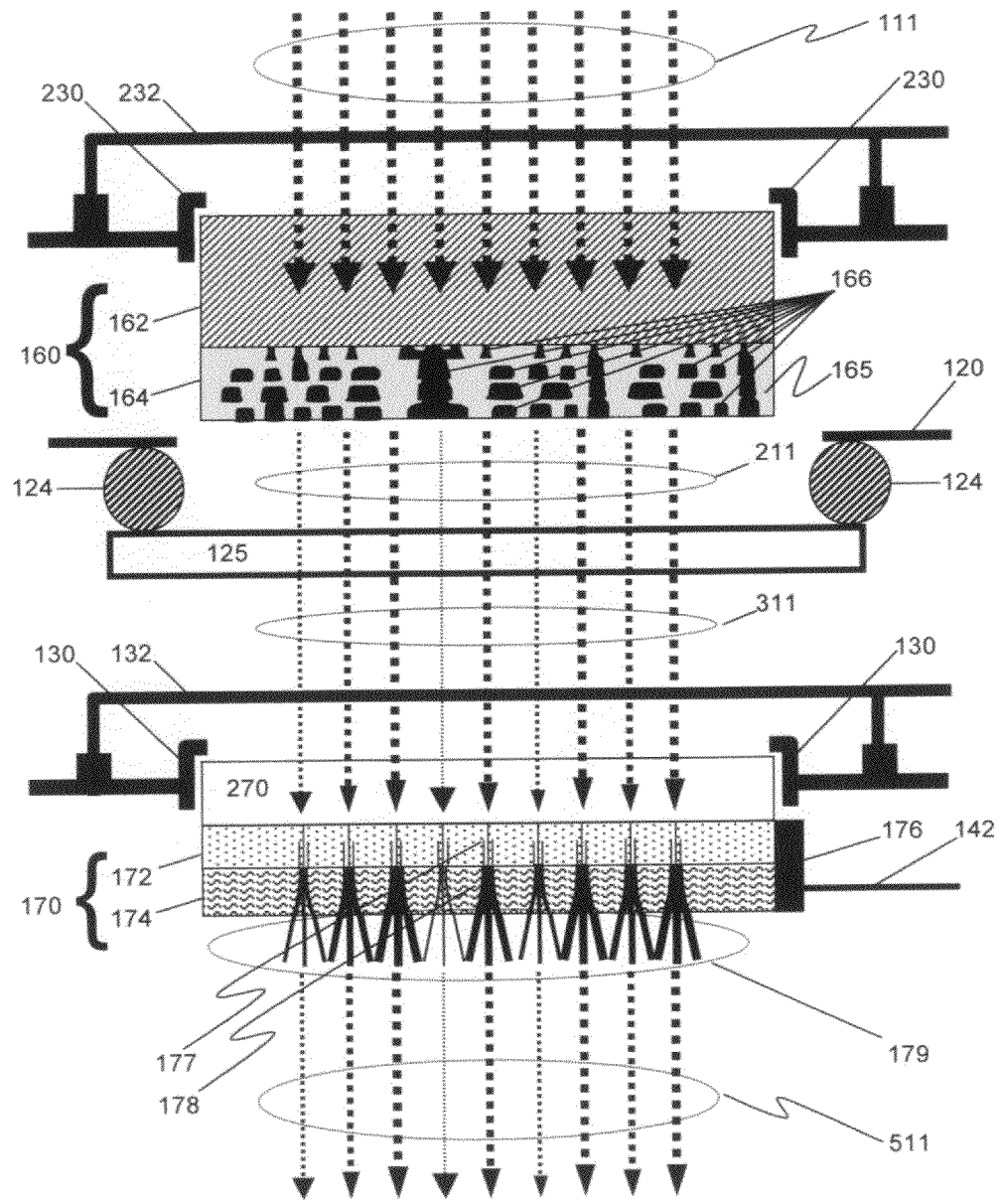
FIG. 4 illustrates a detailed cross-section view of the integrated device and photoemissive structure for the embodiment illustrated in FIG. 3.
Figure 5:
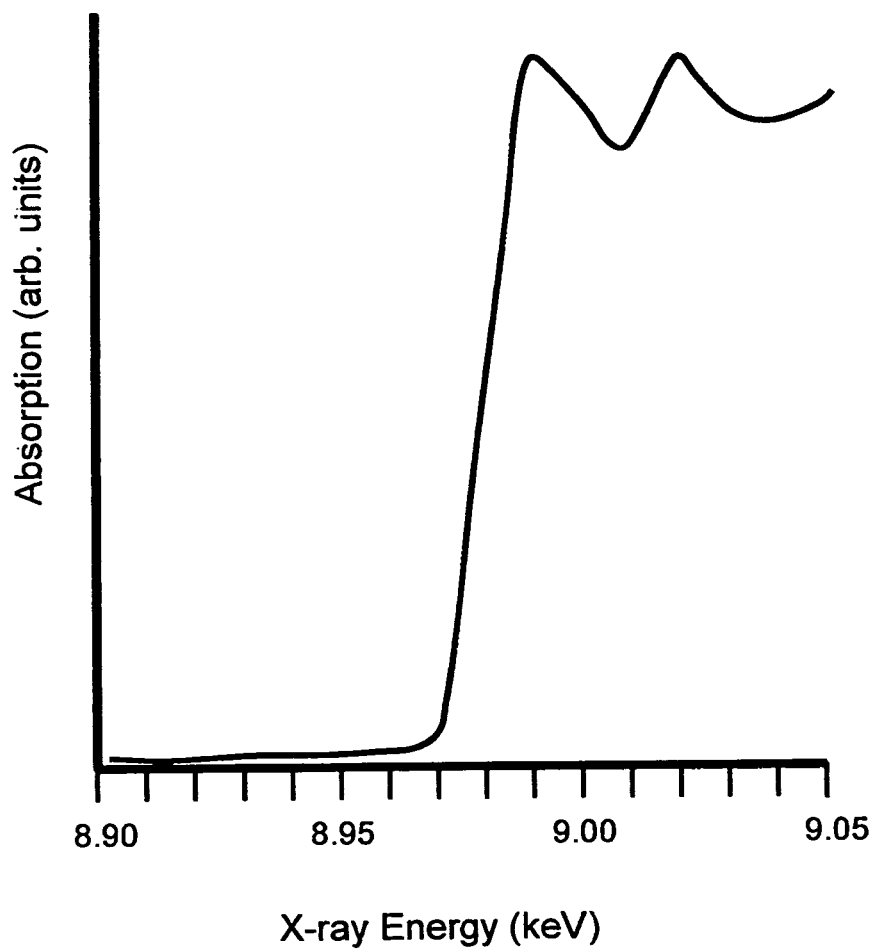
FIG. 5 illustrates a typical copper x-ray absorption spectrum.
Figure 6:
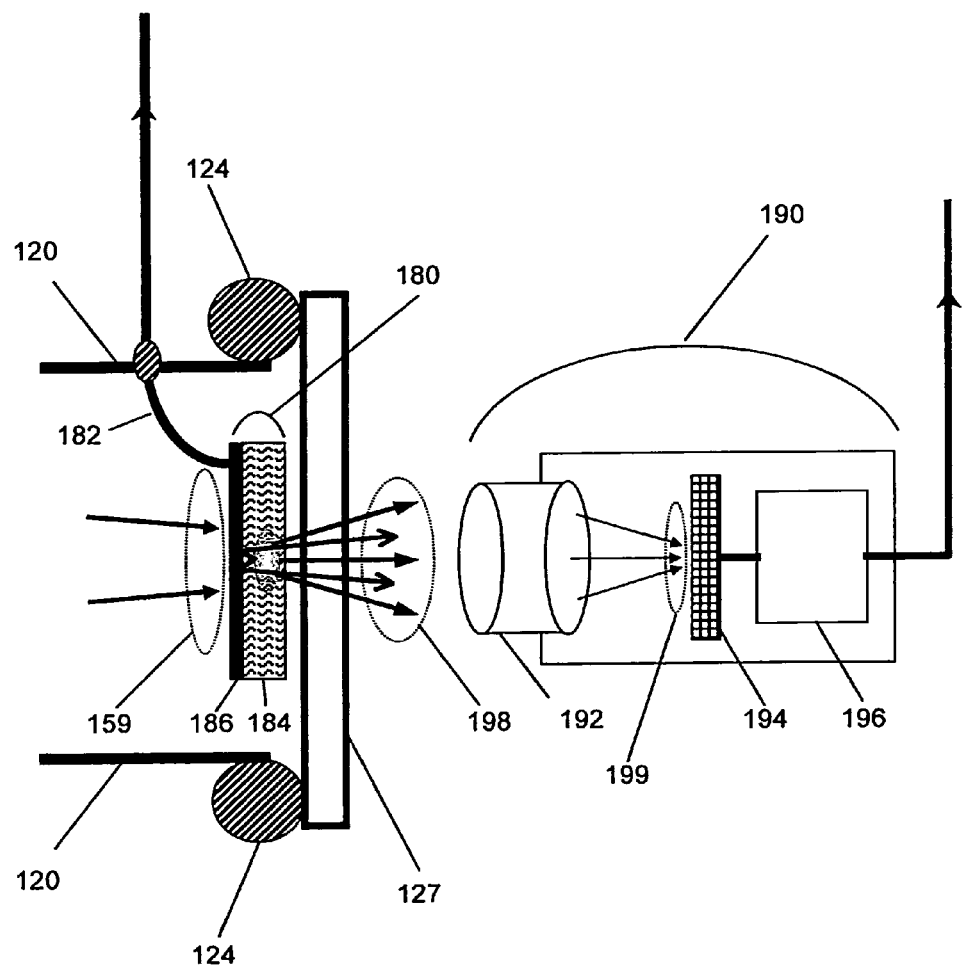
FIG. 6 illustrates a detailed cross-section view of the electron image converter and imaging system for the embodiment illustrated in FIG. 3.
Figure 7:
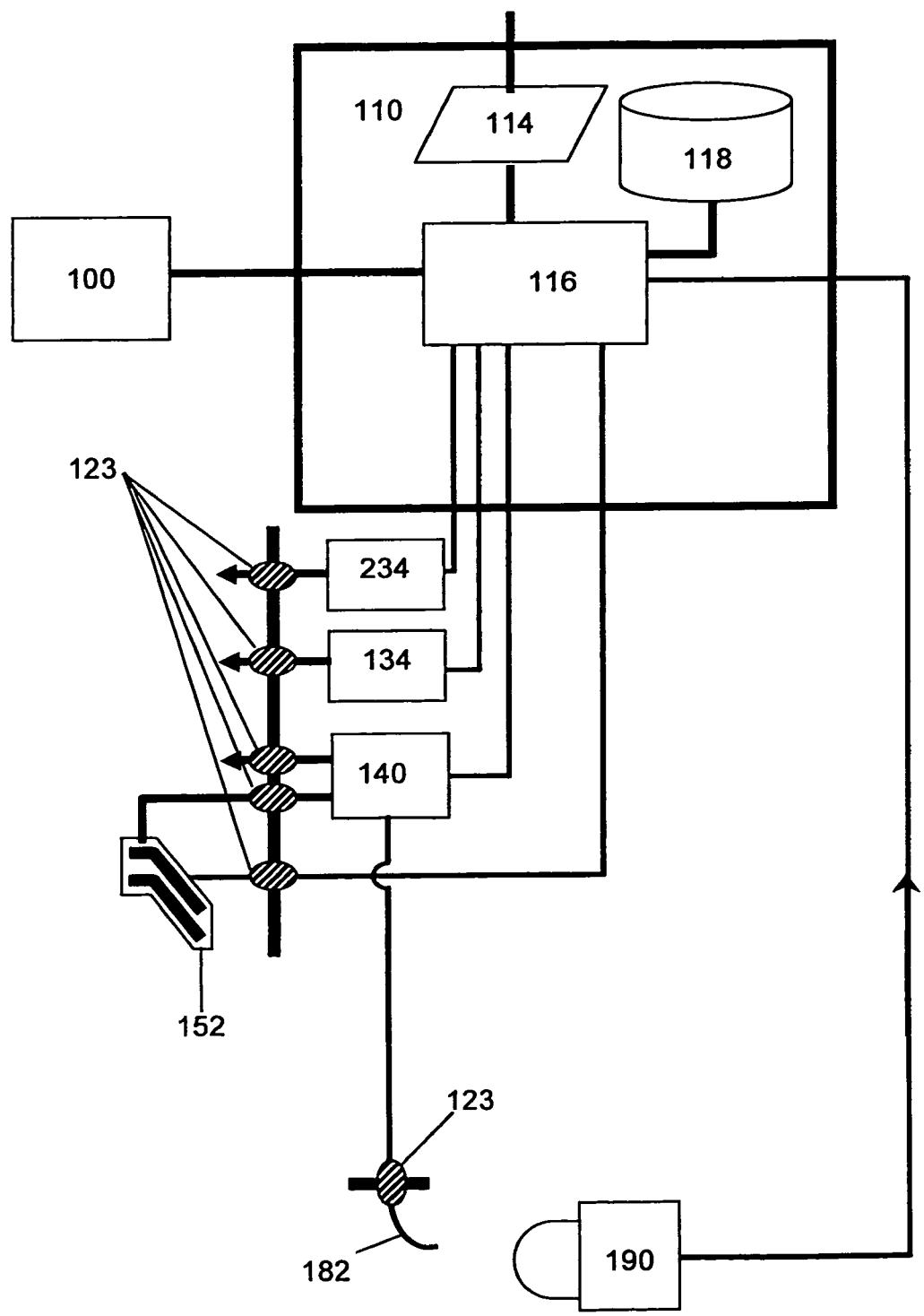
FIG. 7 illustrates a schematic of the control systems to be used for the embodiment illustrated in FIG. 3.

One embodiment of the apparatus according to the invention for the examination of an integrated device 160 is illustrated in FIG. 3 through FIG. 7. FIG. 3 illustrates a cross section view of the overall system. FIG. 4 illustrates a cross-section in detail of the integrated device 160 and photoemissive structure 170. FIG. 5 illustrates the x-ray energy absorption for copper, used in many integrated devices. FIG. 6 illustrates a cross section in detail of the image converter 180 and the imaging system 190. FIG. 7 illustrates a schematic of the various elements connected to the system controller 110.

Turning first to FIG. 3, the apparatus comprises a source of x-rays 100 and also comprises beam-shaping optics 104 which provide a beam of x-rays 111, directed onto the integrated device 160, with a predetermined energy (i.e. wavelength) spectrum and a predetermined angular distribution. The energy spectrum can be a broad emission spectrum, or filtered to have a specific set of wavelengths, or can comprise some other combination of wavelengths. Likewise, the angular distribution can be a diverging beam, a converging beam, or a collimated beam.

The source of x-rays 100 can be any x-ray source, including a synchrotron, a fixed target x-ray tube, a rotating anode source, a laser plasma source, or other sources that will be well known to those skilled in the art. The source of x-rays 100 can be operated to continuously emit x-rays, or be operated in a pulsed mode. The beam shaping optics 104 can comprise any of a number of x-ray beam shaping tools, including capillary collimators, grazing incidence reflecting cones, and zone plates. However, a beam of x-rays for this system would generally have a numerical aperture of approximately nine milliradians (9 mrad).

The system further comprises a vacuum chamber 120 and a means of establishing a vacuum 121 within the vacuum chamber 120, such as a vacuum pump. The means of establishing a vacuum 121 may use a valve 122 for vacuum control, which in some embodiments of the invention can allow the vacuum chamber to be detached from the means of creating a vacuum 121 once the vacuum is established. Additionally, the wall of the vacuum chamber 120 may comprise junctions 123 to preserve vacuum at any mechanical or electrical access points in the system, and vacuum seals 124 at other access points such as windows.

In this embodiment of the invention, on the side of the system exposed to the beam of x-rays 111, the integrated device 160 is mounted outside the vacuum chamber 120, using an external stage 230. The external stage 230 may be attached to the vacuum chamber 120 or, in some embodiments, may be independently supported and not in physical contact with the vacuum chamber. In some embodiments of the invention, this external stage 230 will be fixed in place, and in others the external stage 230 may have external stage controls 232 to adjust position and orientation. Adjustments enabled for the external stage 230 through the controls 232 may include motion in the x-y plane perpendicular to the axis of propagation of the x-rays; it may also include rotation about the x- or y-axis, and it may also include translation in the z-axis along the axis of propagation of the x-rays, and may also include rotation around the z-axis. It may also include rotation and/or translation about any axis or axes.

Adjustment of the external stage controls 232 can be governed by an external stage controller 234, which is generally a system of electronics also outside the vacuum chamber 120. In some embodiments, this external stage controller 234 can in turn be controlled by the overall system controller 110, which can designate an organized scan of positions and orientation angles of the external stage 230 to facilitate the examination of the entire integrated device 160 at multiple exposure angles. These controls may make it possible for a relatively small beam of x-rays to be used to examine the entire area of an integrated device 160 much larger than the diameter of the x-ray beam 111.

After passing through the integrated device 160, the intensity of the beam of x-rays 111 will be modified by the absorption or scattering of x-rays within the integrated device 160. The modified x-ray beam 211 enters the vacuum chamber 120 through an entrance window 125, made from a material selected to be relatively transparent to x-rays, such as beryllium or diamond. It is desired that this be a uniform material, so that the intensity profile of the internal modified beam of x-rays 311 (i.e. inside the vacuum chamber 120) is proportional and nearly identical to that of the external modified beam of x-rays 211.

Once inside the vacuum chamber 120, the internal modified beam of x-rays 311 will encounter a photoemissive structure 170. Some x-rays will be absorbed by the photoemissive structure 170, while the remaining unabsorbed beam of x-rays 511 exits the photoemissive structure 170 and proceeds on into the vacuum chamber 120. In some embodiments of the invention, the unabsorbed beam of x-rays 511 will eventually be absorbed by a beam dump 108 elsewhere in the vacuum system.

The absorption of x-rays in this structure stimulates the emission of electrons 179 from the photoemissive structure 170. However, since the elements of the photoemissive structure 170 are often thin films, in some embodiments of the invention a support structure 270 may also be used provide additional mechanical support for the photoemissive structure 170. Care should be taken in the selection of materials for the support structure 270 so that significant distortions to the internal modified beam of x-rays 311 are not introduced.

The support structure 270 and photoemissive structure 170 can be supported and adjusted using a stage 130 within the vacuum chamber 120. This stage 130 may be attached to the vacuum chamber 120, as illustrated in FIG. 3. In some embodiments of the invention, this stage 130 will be fixed in place, and in others the stage 130 may have stage controls 132 to adjust position and orientation. Adjustments enabled for the stage 130 may include motion in the x-y plane perpendicular to the axis of propagation of the x-rays; it may also include rotation about the x- or y-axis, and it may also include translation in the z-axis along the axis of propagation of the x-rays, and may also include rotation around the z-axis.

Adjustment of the stage controls 132 can be governed by a stage controller 134, which is generally a system of electronics also outside the vacuum chamber 120. In some embodiments, this stage controller 134 can in turn be controlled by the overall system controller 110, which can designate an organized scan of positions and angles of the stage 130 to improve the signal from the emitted electrons 179.

FIG. 4 shows a detailed cross-section view of this embodiment of the integrated device 160 and photoemissive structure 170 according to the invention in more detail. A typical integrated device 160, such as an integrated circuit, will comprise a substrate 162 of a material, such as silicon, on which a layer comprising integrated structures 164 has been fabricated. The devices will often be in the form of a plurality of structures, often fabricated in several planar processing steps that form devices and the structures interconnecting them. The illustration of FIG. 4 shows a cross-section of a representation of a layer comprising integrated structures 164 which contains many structures fabricated using 4 planar layers, which include dielectric material 165, shown as grey, and numerous metal interconnect structures 166, shown as black. For simplicity, only a few structures have been illustrated in FIG. 4, but for many contemporary integrated circuits, the metal interconnect structures are often manufactured using copper and the number of metal interconnect structures number in the billions. Typical overall x- and y-dimensions for an integrated device 160 may be 1 cm×1 cm, while the dimensions of the interconnect structures 166 are often smaller than 100 nm, and can be as small as 20 nm in a contemporary integrated circuit.

For some embodiments of the invention, especially when used to observe copper interconnect structures, the energy of the beam of x-rays 111 can be selected so that a significant portion of the x-rays have energy greater than the energy of the copper K-band absorption edge. FIG. 5 illustrates a graph showing a typical plot of the copper x-ray absorption near edge structure (XANES) absorption spectrum. When the spectrum of x-ray energy for the beam of x-rays 111 is chosen to have a significant fraction above the copper K-band absorption at 8.98 eV, the copper structures will strongly absorb many of the x-rays, while the other dielectric structures will transmit the x-rays. This will result in the varying degrees of x-ray transmission through the integrated device and therefore improved contrast. The external modified beam of x-rays 211 will therefore have a strongly varying intensity profile, representing copper interconnect structures.

Returning to FIG. 4, The photoemissive structure 170 may comprise a layer 172 of photoemissive material that generates a cascade of electrons 177 when irradiated with x-rays. This layer 172 can be fabricated using a material such as gold, but other photoemissive materials will be known to those skilled in the art of electron—material interactions. It is desired that the composition of the material of this layer 172 be relatively uniform, so that the cascade of electrons 177, comprising primary electrons generated by the x-rays and also secondary electrons generated in turn by the primary electrons, has an electron density that is in proportion to the local flux of x-rays passing through the material.

The thickness of the layer 172 must also be selected with care, as a layer 172 that is too thin may not generate a strong cascade of electrons 177, while a layer 172 that is too thick may generate a cascade of electrons 177 whose number is no longer in proportion to the flux of incident x-rays. In one embodiment of the invention, layer 172 is fabricated using gold having a thickness of approximately 50 nm.

Once the cascade of electrons 177 is generated, some of these electrons exit the layer 172 of photoemissive material. However, in some cases, the material used to fabricate the layer 172 of photoemissive material may be selected to have the capability of generating a large number of electrons from a few absorbed x-rays, but which may also have a large work function. This may reduce the emission of some of the generated electrons, which can lead to a reduction in the overall signal strength.

Therefore, in some embodiments of the invention, it is desired that the photoemissive structure 170 additionally comprise an emissive coating 174. The material used to fabricate this emissive coating 174 can be chosen to have a low work function, so that it is more likely that the cascade of electrons 177 initiated by the x-ray exposure in the layer 172 of photoemissive material will result in a large number of emitted electrons 179. The material used for the emissive coating 174 can also be chosen so that the electrons of the cascade of electrons 177 that are transferred into the emissive coating 174 can generate additional secondary electrons, forming an amplified electron cascade 178. Materials such as cesium iodide (CsI), which has a low work function and good electron generation properties, may be used for the emissive coating 174 in some embodiments of the invention. In one embodiment of the invention, the emissive coating 174 is a CsI layer with a thickness of 100 nm. In another embodiment of the invention, the emissive coating 174 is a CsI layer with a thickness of 5 nm.

Returning to FIG. 3, in some embodiments of the invention, there will be a voltage applied to the photoemissive structure using electrical contact 176 and electrical lead 142. The relative voltage compared to the voltage applied to the subsequent electron optics, such as cathode lens 152, will be set such that the emitted electrons 179 are accelerated away from the surface of the photoemissive structure 170 towards the electron optics.

It will be known to those skilled in the art that other architectures for the photoemissive structure can be designed comprising additional layers, and in which voltage differences between the layers of the photoemissive structure 170 are established as well, to accelerate the electrons between the layers of the photoemissive structure 170.

Some embodiments of the invention will have a voltage controller 140 that uses electrical lead 142, connecting to the photoemissive structure 170, and cathode lens electrical lead 144, connecting to the cathode lens 152, to set the relative voltage of the photoemissive structure 170 and the cathode lens 152. If the voltage provided through the lead 142 to the electrical contact 176 is significantly more negative than the voltage provided through the lead 144 to the cathode lens, then the emitted electrons 179 will be accelerated away from the photoemissive structure 170 and into the electron optical system. In some embodiments of the invention, a voltage difference of twenty kilovolts (20 kV) will be established between electrical lead 142 and cathode lens electrical lead 144. In another embodiment of the invention, a voltage difference of fifty kilovolts (50 kV) will be established.

A typical electron optical system comprises a combination of electron optics, such as the cathode lens 152, apertures 154, beam steering optical elements 156 and transfer and projection lenses 158. The electron optics can be positioned inside the vacuum chamber 120, such as when the electron optical design uses electrostatic lenses, or be positioned outside the vacuum chamber 120, such as when magnetic lenses are used, as illustrated in FIG. 3. The optics can also be configured to be adjustable for imaging properties such as astigmatism and other aberration corrections, and in particular to adjust the position and orientation of the cathode lens 152 relative to the photoemissive structure 170. These can be predetermined adjustments, or may be adjusted by signals from the system controller 110 in response to feedback about the imaging performance of the system. In some embodiments of the invention, the stage controls 132 may be used on the stage 130 holding the photoemissive structure 170 to adjust the position and orientation of the photoemissive structure 170 relative to the electron optics and the optical axis of the electron optics.

In some embodiments of the invention, the electron optics will comprise beam steering optical elements 156 so that the emitted electrons 179 are no longer co-linear with the unabsorbed beam of x-rays 511. This allows the unabsorbed beam of x-rays 511 to fall into a beam dump 108, where it is absorbed and therefore prevented from leaving the vacuum chamber, reducing the risk of inadvertent radiation exposure.

In some embodiments of the invention, the various electron optical elements form a magnified electron image 159 of the emitted electrons 179 in the final image plane of the electron optical system. In some embodiments, the magnified electron image 159 will be 150 times larger than the pattern of emitted electrons 179. In other embodiments, the magnified electron image 159 will be 1,500 times larger than the pattern of emitted electrons 179.

The electron optical system will typically be designed such that the image plane is within the vacuum chamber 120. An image converter 180 is placed at this image plane that emits photons 198 when excited by energetic electrons of the magnified electron image 159. These photons 198 are generally visible photons (i.e. with a wavelength between 400-700 nm), although in some embodiments the emitted photons 198 may be infrared or ultraviolet photons. Some of the emitted photons 198 from the image converter 180 exit the vacuum chamber 120 through exit window 127, and are collected by the imaging system 190. In some embodiments, this imaging system 190 comprises a video system or a CCD array to create electronic signals corresponding to the emitted photons 198.

FIG. 6 illustrates a detailed cross-section view of the structure of the image converter 180 and imaging system 190 for this embodiment of the invention. In this embodiment, the image converter 180 comprises a scintillator 184. Such scintillators are common in electron microscopy, and many variations containing a variety of phosphors that emit photons when stimulated with energetic electrons will be known to those skilled in the art. The scintillator 184 can comprise a phosphorescent material, such as zinc sulfide (ZnS) doped with manganese (Mn) or other elements, a structure comprising a crystal material such as Yttrium Aluminum Garnet (YAG), or compositions comprising various rare earth elements. The fabrication of the image converter 180 should result in a uniform structure of material in the scintillator 184, so that the intensity of the emitted photons 198 is in proportion to the number of incident electrons absorbed from the magnified electron image 159.

In some embodiments, the image converter 180 may comprise additional layers, such as a conducting layer 186 on the side of the image converter 180 on which the electrons of the magnified electron image 159 are incident. In some embodiments of the invention, this conducting layer 186 can be attached electrically using an electrical lead 182 to set the image converter 180 to a specific voltage. In some embodiments of the invention, the specific voltage on the electrical lead 182 will be set to zero volts, and the lead 182 therefore provides a path to ground for the absorbed electrons of the magnified electron image 159. In some embodiments, the voltage may be set by voltage controller 140. In some embodiments, the conducting layer 186 is fabricated using a material that reflects photons such as a metallic thin film. In some embodiments, the conducting layer 186 will be approximately 50 nm thick, and fabricated using a material comprising aluminum. This provides an additional benefit of taking any photons from the scintillator 184 emitted in the direction of the incoming electrons and reflecting them back towards the exit window 127, where they add to the intensity of the emitted photons 198.

Outside the vacuum chamber, an imaging system 190 can be used to produce an image 199 of the emitted photons 198. In some embodiments, this imaging system 190 comprises a lens system 192, an image sensor 194, and image processing electronics 196 that can be used to convert the image 199 of the emitted photons 198 into electronic signals. In some embodiments, the lens system 192 forms a magnified image of the emitted photons 198. In some embodiments, this magnification is by a factor of 100. In some embodiments, the image sensor 194 will be a charge-coupled device (CCD) array. In some embodiments, the signals will be a represent the image using video formats. In other embodiments, these signals will be a collection of still images.

If the materials of the photoemissive structure 170 and the image converter 180 are well selected and uniformly fabricated, and the adjustments of the electron optics 152, 156 and 158 are made to minimize aberrations and distortions, the final electronic signals from the imaging system 190 will represent a magnified image of the x-ray transmission of the corresponding portion of the integrated device 160.

FIG. 7 illustrates in more detail a schematic of the control systems to be used for some embodiments of the invention. The electronic images generated by the imaging system 190 can be transmitted to the system controller 110. This controller 110 can comprise a means for governing the source of x-rays 100, such as adjusting the x-ray intensity, pulsing the source, or making adjustments to the beam shaping optics 104 to collimate or concentrate the beam.

This controller 110 can further comprise a means for electronic input and output 114.

This controller 110 can further comprise an electronic processor 116. This processor 116 may be programmed to manage the external stage controller 234 that drives the external stage controls 232 that adjust the position and orientation for the external stage 230 supporting the integrated device 160. This processor 116 may also be programmed to manage the stage controller 134 that drives the stage controls 132 that adjust the position and orientation for the stage 130 supporting the photoemissive structure 170. This processor 116 may be programmed to manage the voltage controller 140 that adjusts the relative voltage of the photoemissive structure 170 and the cathode lens 152, and may also control the voltage setting for the electrical lead 182 for the scintillator 184. This processor 116 may also be programmed to adjust the settings and aberration controls of the cathode lens 152.

In some embodiments of the invention, the controller 110 will also comprise electronic data storage 118, which can be used to record the position and orientation set for the external stage 230, the stage 130, and the control voltages for the photoemissive structure 170 and image converter 180, as well as the corresponding images collected by the imaging system 190.

In some embodiments, the information and signals representing images recorded in the electronic data storage 118 can be combined to synthesize a two-dimensional (2-D) or three-dimensional (3-D) representation of the integrated device 160 or portions thereof.

In some embodiments of the invention, these synthesized 2-D or 3-D representations can be compared with a stored representation of an integrated device known to be correctly manufactured, or a database representation of the design rules or the layout of the device as designed, and the resulting comparison used to evaluate the attributes of the integrated device 160 being examined. Such a system can be used as an inspection system for manufacturing quality control.

Second Embodiment of the Invention

Figure 8:
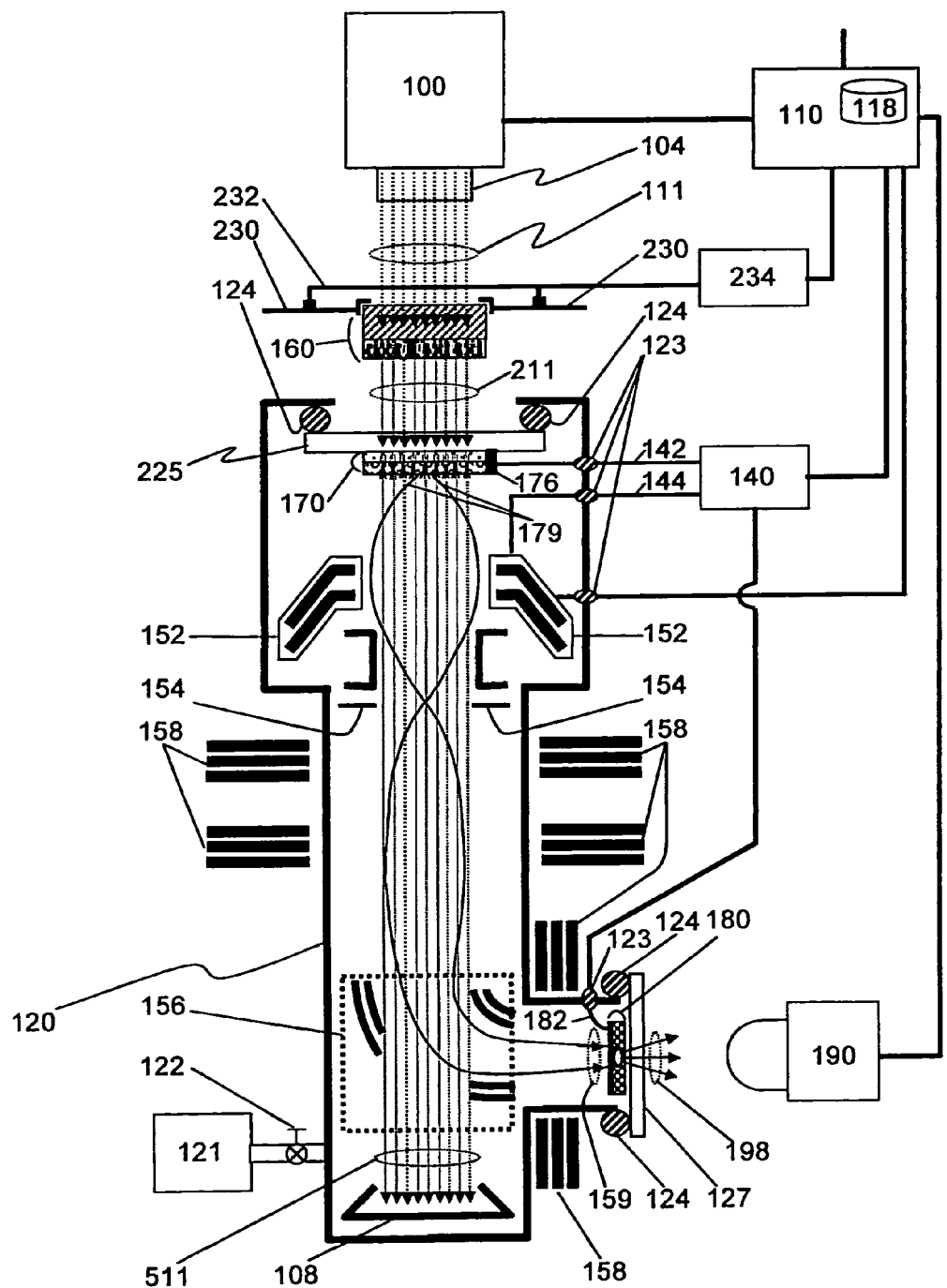
FIG. 8 illustrates a cross-section view of a microscope system according to a second embodiment of the invention, in which the integrated device is outside the vacuum chamber and the photoemissive structure is coated onto the window of the vacuum chamber.
Figure 9:
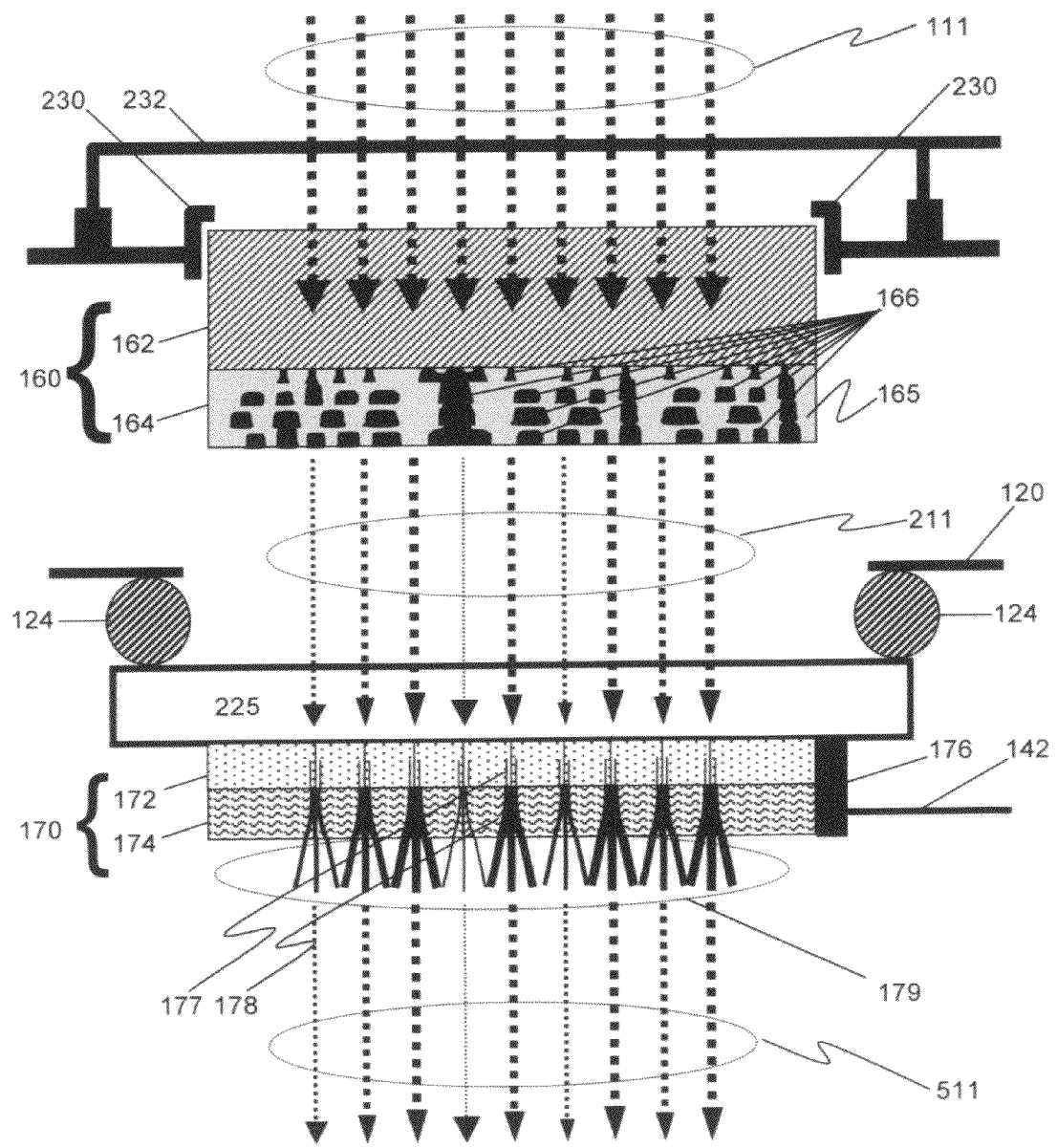
FIG. 9 illustrates a detailed cross-section view of the integrated device and photoemissive structure for the embodiment illustrated in FIG. 8.

FIG. 8 and FIG. 9 illustrate another embodiment of an apparatus according to the invention. FIG. 8 illustrates a cross section view of the overall system, and FIG. 9 illustrates a cross-section in detail of the integrated device 160 and photoemissive structure 170.

As in the previously described embodiment of the invention, an x-ray source 100 produces a beam of x-rays 111 which are partially absorbed by the integrated device 160 under examination, forming a modified beams of x-rays 211.

As in the previously described embodiment of the invention, the integrated device 160 is mounted outside the vacuum chamber 120, using an external stage 230. In some embodiments of the invention, this external stage 230 will be fixed in place, and in others the external stage 230 may have external stage controls 232 to adjust position and orientation. Adjustment of the external stage controls 232 can be governed by an external stage controller 234, which is generally a system of electronics also outside the vacuum chamber 120. In some embodiments, this stage controller 234 can in turn be controlled by the overall system controller 110, which can designate an organized scan of positions and angles of the external stage 230 to facilitate the examination of the integrated device 160.

After passing through the integrated device 160, the modified beam of x-rays 211 enters the vacuum chamber 120. However, in this embodiment of the invention, the photoemissive structure 170 has been fabricated directly onto the support window 225 of the vacuum chamber 120. The support window 225 may be similar in design and fabrication to the window 125 described in the previous embodiment, and will also be made using a material transparent to x-rays, such as beryllium or diamond, but may also need to be of a different thickness or composition to serve as both a window for the vacuum chamber 120 and also as a mechanical support for the photoemissive structure 170.

This configuration has some advantages, in that the need for stage 130, stage controls 132 and stage controller 134 inside the vacuum chamber are eliminated, along with the corresponding feedthrough junctions 123. Also, the need to select two materials, the window 125 and the support structure 270, for mechanical and x-ray transmission properties is simplified to the selection of a single material for support window 225.

In some embodiments of the invention, a vacuum chamber may be designed in which the position and orientation of the window can also be adjusted relative to the electron optics and the optical axis of the electron optics. However, since windows for vacuum systems are typically fixed in place, in the embodiment as illustrated here, the photoemissive structure 170 also becomes fixed in position and orientation. Any relative changes in position or orientation angle between the integrated device 160 and the photoemissive structure 170 would then need to be controlled through the position and orientation of the external stage 230 for the integrated device 160.

Likewise, because the support window 225 will function as a seal for the vacuum chamber 120 and therefore be near or in contact with the walls of the vacuum chamber 120, care must be taken in setting the voltage for electrical lead 142 relative to the electron optics so that electrical shorting through to vacuum chamber 120 does not occur.

As in the previously described embodiment of the invention, after transmission through the photoemissive structure 170, the unabsorbed beam of x-rays 511 can proceed in the vacuum chamber 120 to a beam dump 108 where it is absorbed.

As in the previously described embodiment of the invention, the emitted electrons 179 are directed by a set of electron optics to form a magnified image 159 at an image converter 180. As in the previous embodiment of the invention, the photons 198 emitted by the image converter 180 leave the vacuum chamber through exit window 127 and are converted to electronic signals in imaging system 190. These are transmitted to a controller 110, which can record these images using electronic data storage 118.

As in the previously described embodiment of the invention, the information and signals representing images recorded in the electronic data storage 118 can be combined to synthesize a two-dimensional (2-D) or three-dimensional (3-D) representation of the integrated device 160 or portions thereof.

As in the previously described embodiment of the invention, these synthesized 2-D or 3-D representations can be compared with a stored representation of an integrated device known to be correctly manufactured, or a database representation of the design rules or the layout of the device as designed, and the resulting comparison used to evaluate the attributes of the integrated device 160 being examined. Such a system can be used as an inspection system for manufacturing quality control.

Third Embodiment of the Invention

Figure 10:
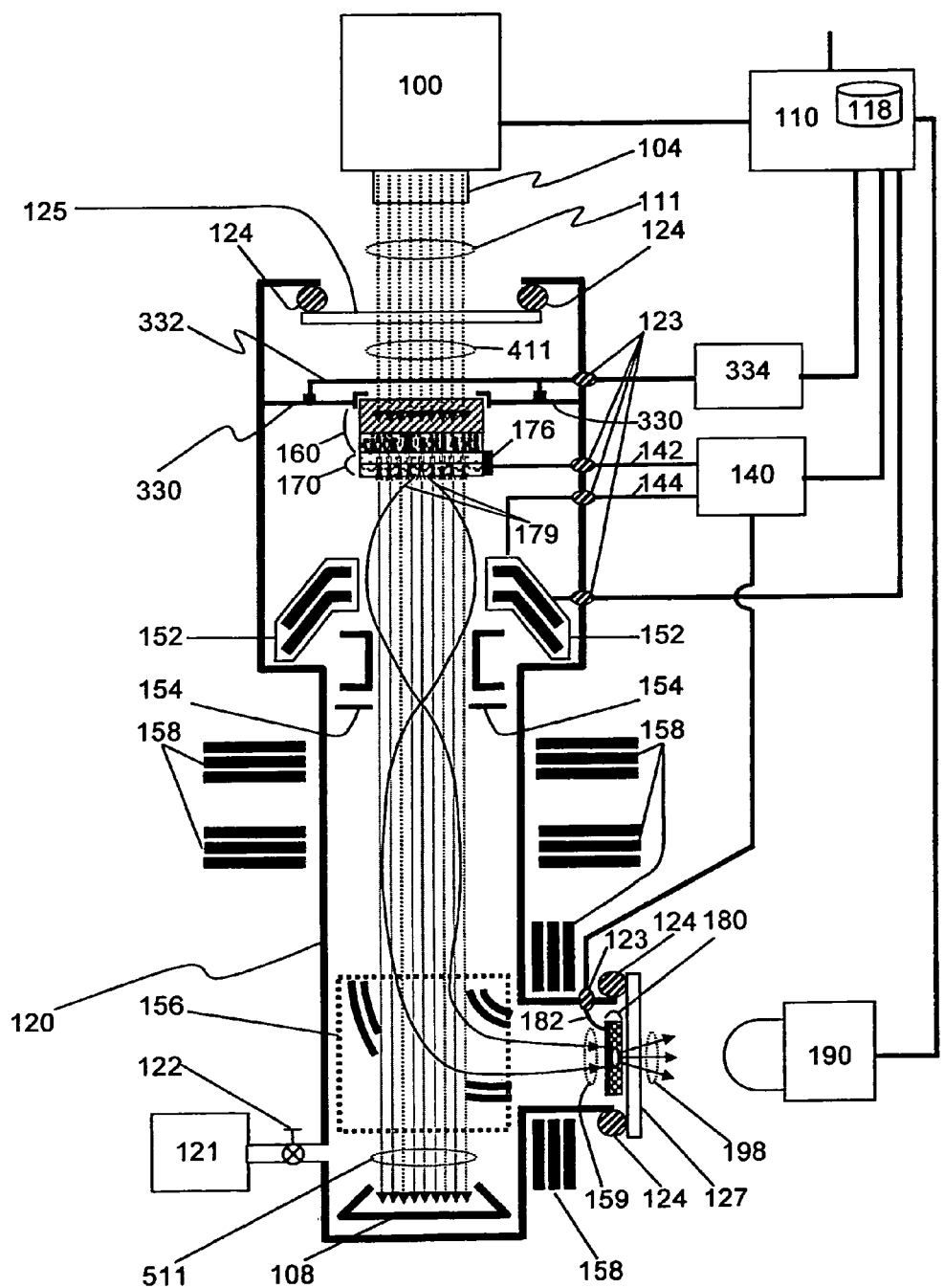
FIG. 10 illustrates a cross-section view of a microscope system according to a third embodiment of the invention, in which the integrated device is inside the vacuum chamber and the photoemissive structure is coated onto the integrated device.
Figure 11:
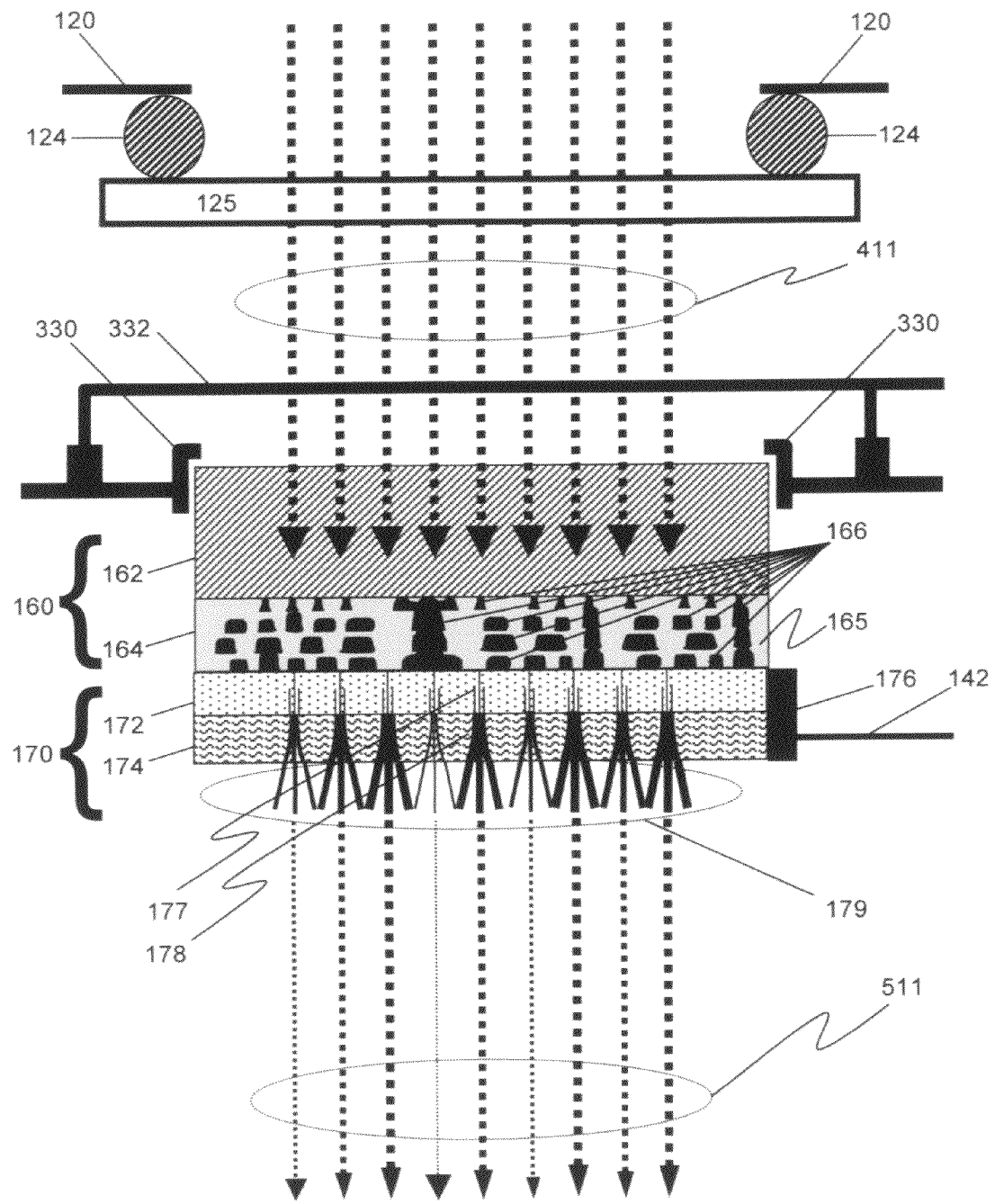
FIG. 11 illustrates a detailed cross-section view of the integrated device and photoemissive structure for the embodiment illustrated in FIG. 10.
Figure 12:
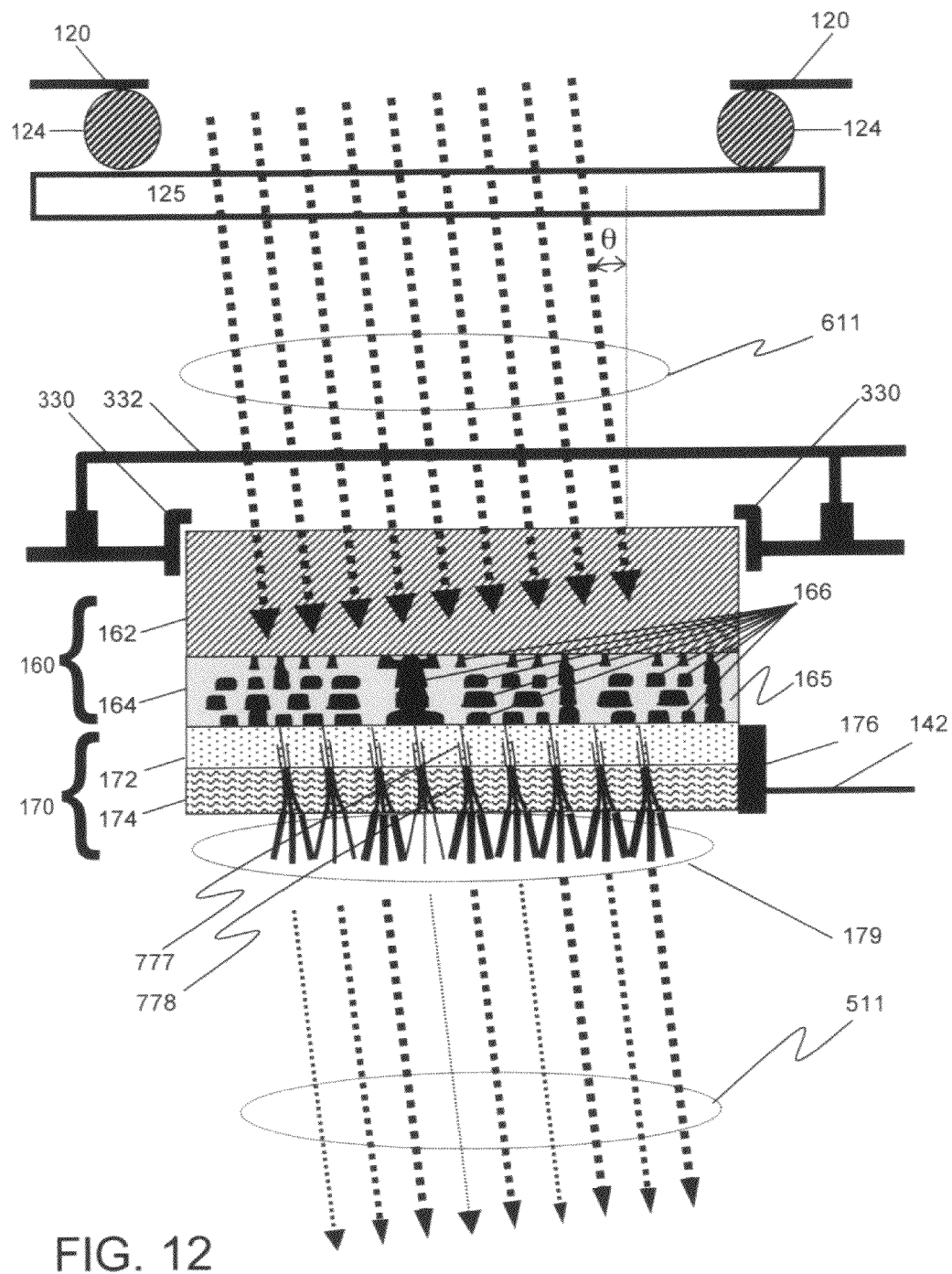
FIG. 12 illustrates a detailed cross-section view of the integrated device and photoemissive structure for a variation of the embodiment illustrated in FIG. 10 in which the angle of incidence is variable.
Figure 13:
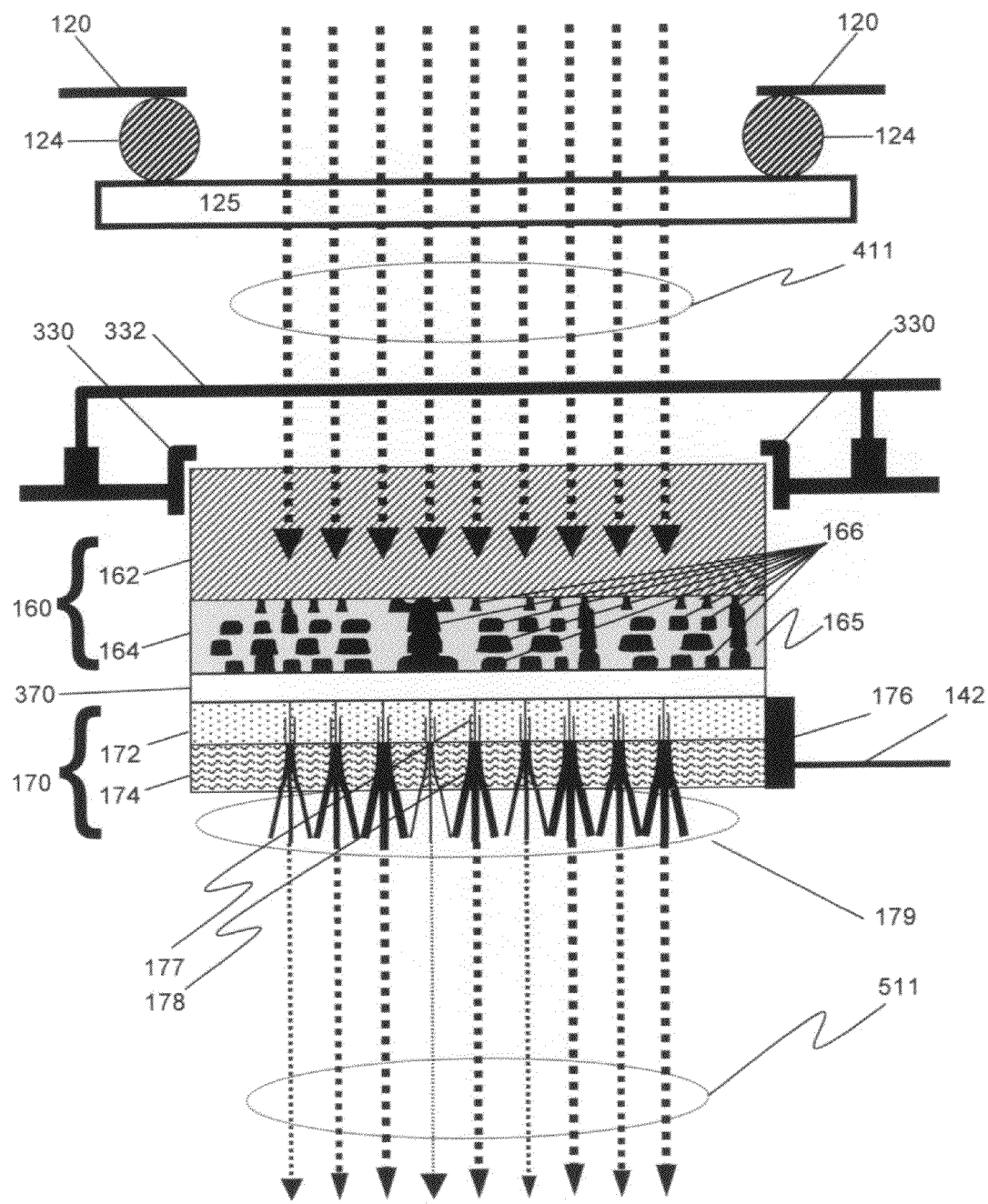
FIG. 13 illustrates a detailed cross-section view of the integrated device and photoemissive structure for a variation of the embodiment illustrated in FIG. 10.

FIG. 10 through FIG. 13 illustrate another embodiment of an apparatus according to the invention. FIG. 10 illustrates a cross-section view of the overall system, and FIG. 11 illustrates a cross-section in detail of the integrated device 160 and photoemissive structure 170. FIG. 12 and FIG. 13 each illustrate a cross-section in detail of the integrated device 160 and photoemissive structure 170 for two different variations of the embodiment.

As in the previously described embodiments of the invention, an x-ray source 100 produces a beam of x-rays 111. In this embodiment, however, the beam of x-rays directly enters the vacuum chamber 120 through the entrance window 125 without passing through the integrated device 160, becoming the interior unmodified beam of x-rays 411. The modifications that make the interior unmodified beam of x-rays 411 different from the incident beam of x-rays 111 are only due to absorption and scattering from the window 125.

In this embodiment, the photoemissive structure 170 is deposited directly onto the integrated device 160 to be examined. Both the integrated device 160 and the attached photoemissive structure 170 are entirely contained within the vacuum chamber 120. Therefore, the need for external stage 230, external stage controls 232, and external stage controller 234 are eliminated. However, stage 330 within the vacuum chamber 120 is now used to hold both the integrated device 160 and the photoemissive structure 170, and to adjust their positions and orientation angle relative to the interior beam of x-rays 411 as well. The design of the stage 330 and the stage controls 332 may be very similar to the stage 130 and stage controls 132 in the previous embodiments. However, the additional thickness and support requirements for holding both the integrated device and the photoemissive structure may require some variation in design.

In some embodiments, both the position and the orientation of the integrated device 160 may be adjustable using stage controls 332 for the stage 330, making it possible for a relatively small beam of x-rays to be used to examine the entire area of an integrated device 160 much larger than the diameter of the slightly modified x-ray beam 411. Adjustment of the stage controls 332 can be governed by a stage controller 334, which is generally a system of electronics outside the vacuum chamber 120. In some embodiments, this stage controller 334 can in turn be controlled by an overall system controller 110, which can designate an organized scan of positions and angles of the stage 130 to facilitate the examination of the integrated device 160. In some embodiments of the invention, the stage controls 332 may be used on the stage 330 holding the integrated device 160 and photoemissive structure 170 to adjust the position and orientation of the photoemissive structure 170 relative to the electron optics and the optical axis of the electron optics.

As in the previously described embodiments of the invention, the photoemissive structure 170 may comprise a layer 172 of photoemissive material and an emissive coating 174. However, in this embodiment the need for an additional support structure 270 for the photoemissive structure 270 is eliminated, since the structure 170 has been deposited directly on the integrated device 160.

FIG. 12 illustrates a variation of this embodiment of the invention. In the previously illustrated embodiments, the angle of incidence of the beam of x-rays 111 and therefore also modified x-ray beam 411 is perpendicular (i.e. has an angle of incidence at or near) 90° to the surface of the integrated device 160. In this variation of the embodiment, motion of the x-ray source 100 or adjustment of the beam-shaping optics 104 can provide x-rays incident on the integrated device 160 at some value θ which is not 90°, and in fact in some embodiments may be adjustable to provide a multiplicity of angles of illumination, either simultaneously or in a programmed time sequence. The angled beam of x-rays 611 will have an intensity pattern that is different from the normal incidence case of FIG. 11, and therefore the trajectory and intensity pattern of the cascade of electrons 777 and the amplified electron cascade 778 will be different from the trajectory and intensity pattern of the cascade of electrons 177 and the amplified electron cascade 178 in the normal incidence case of FIG. 11.

However, once the electrons 179 are emitted from the surface of the photoemissive structure 170, they are accelerated towards the cathode lens 152, and a magnified image is formed by the image converter 180 and imaging system 190, as in the previous embodiments of the invention.

Such an embodiment can be used in conjunction with various image processing algorithms such as those for computed laminography, also known as digital tomosynthesis, synthetic laminography, or computerized synthetic cross sectional imaging, in which images from multiple angles are collected to and processed to provide a 3-dimensional representation of the layers of the integrated device 160. In some cases, a simple parallax computation from two images at different angles may be enough to infer 3-D structural information. In other cases in which the basic structure (i.e. layer thicknesses and approximate feature sizes) are known, collecting images for a few multiple angles near perpendicular may provide enough information to infer 3-D detailed structural information.

The advantage of computed laminography algorithms over more commonly used computed tomography (CT) algorithms is that transmission information from a wide range of angles around the sample need not be collected. When the integrated device 160 is in a vacuum chamber requiring a window 125 for x-ray transmission, and the alignment with the electron optics can be delicate, the wide range of motion required by many tomography algorithms can require a system that is mechanically complex. When only a few angles and views are required, the integrated device 160 and photoemissive structure 170 can remain aligned with the electron optics, and even at times immobile, and only the angle of incidence of the beam of x-rays 611 need be changed.

Although we describe the integrated device 160 and photoemissive structure 170 as being in "direct contact" in this embodiment, it will be known to those skilled in the art that there may be some configurations in which it may be best to deposit additional layers of buffer material between the integrated device 160 and the photoemissive structure 170, to provide a more physically flat, chemically neutral, or electrically insulating surface. Such a planarization layer 370 is illustrated in FIG. 13. This may be especially important if particular voltage settings are desired for the electrical lead 142, since the lead may be also in contact or close proximity to the integrated device 160 and the stage 130.

As in the previous embodiments, some x-rays from the unmodified beam of x-rays 411 are absorbed or scattered in the integrated device, and then stimulate the emission of electrons 179 from the photoemissive structure 170.

As in the previously described embodiments of the invention, after transmission through the photoemissive structure 170, the unabsorbed interior beam of x-rays 511 can proceed in the vacuum chamber 120 to a beam dump 108 where it is absorbed.

As in the previously described embodiments of the invention, the emitted electrons 179 are directed by a set of electron optics and form a magnified image 159 at an image converter 180. As in the previous embodiment of the invention, the photons 198 emitted by the image converter 180 leave the vacuum chamber through the exit window 127 and are converted to electronic signals in imaging system 190. These are transmitted to a controller 110, which can record these images using electronic data storage 118.

As in the previously described embodiments of the invention, the information and signals representing images stored in the electronic data storage 118 can be combined to synthesize a two-dimensional (2-D) or three-dimensional (3-D) representation of the integrated device 160 or portions thereof.

As in the previously described embodiments of the invention, these synthesized 2-D or 3-D representations can be compared with a stored representation of an integrated device known to be correctly manufactured, or a database representation of the design rules or the layout of the device as designed, and the resulting comparison used to evaluate the attributes of the integrated device 160 being examined. Such a system can be used as an inspection system for manufacturing quality control.

Other Embodiments of the Invention

Figure 14:
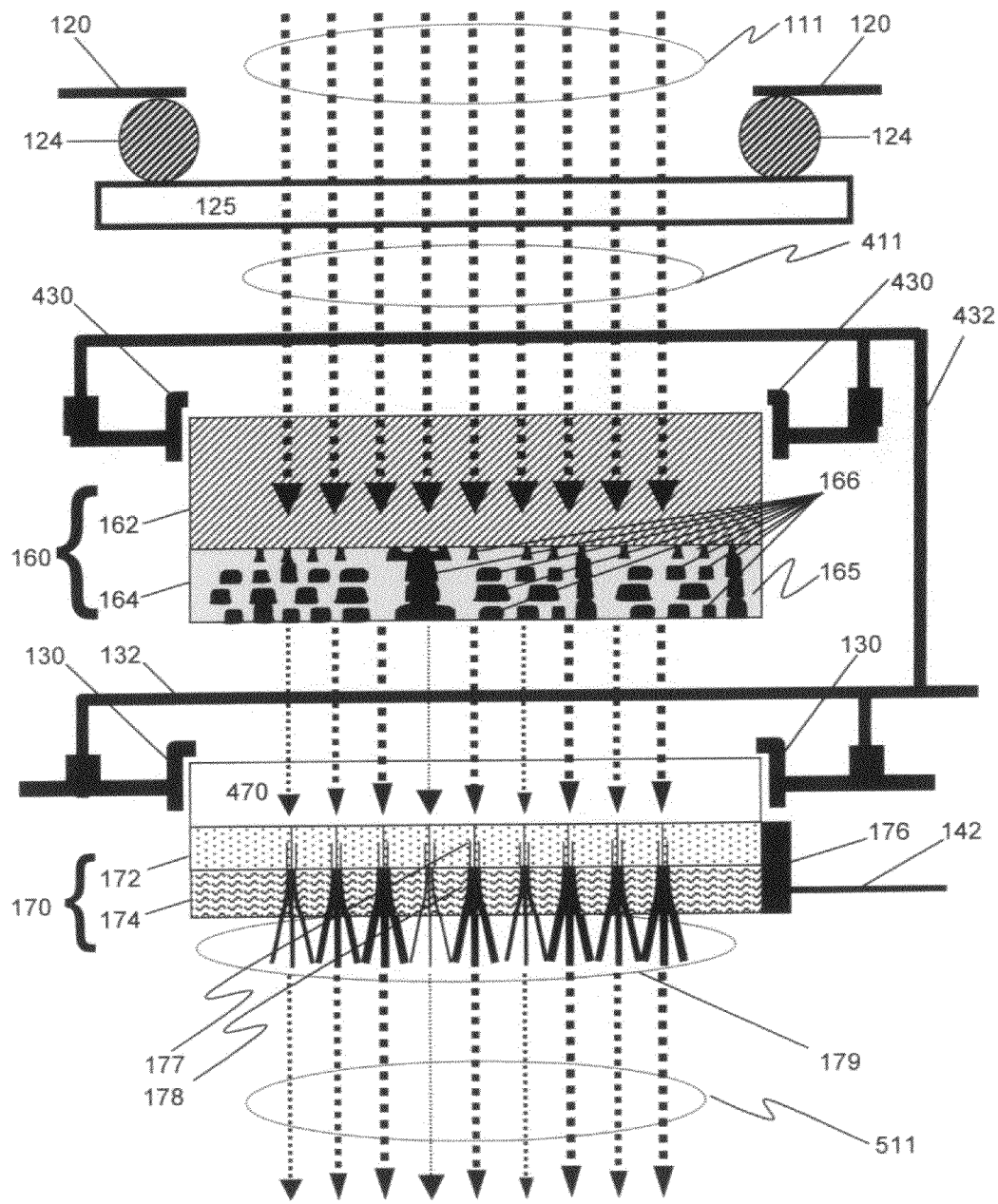
FIG. 14 illustrates a detailed cross-section view of the integrated device and photoemissive structure for a fourth embodiment of the invention.

FIG. 14 illustrates a cross-section in detail of the integrated device 160 and photoemissive structure 170 for another embodiment of an apparatus according to the invention.

In this embodiment, both the integrated device 160 and the photoemissive structure 170 are within the vacuum chamber 120, but the integrated device has a connected stage 430 with connected stage controls 432 that are attached to the stage 130 and stage controls 132 for the photoemissive structure 170. The connected stage 430 may be designed to allow the easy and rapid insertion of integrated devices 160, and to adjust their position and orientation not only with respect to the interior unmodified beam of x-rays 411, but also relative to the photoemissive structure 170. In some embodiments, the connected stage 430 will be designed to allow the integrated device 160 to be moved to be in very close proximity to the photoemissive structure 170. In some embodiments, photoemissive structure also has an independent support 470, which may be similar in design and material composition to the support structure 270 described in the previous embodiments.

The advantage to such a configuration is that the device 160 and the structure 170 can be placed in relatively close proximity, minimizing the distortion from propagation and scattering that can occur with propagation, without actually being in mechanical and electrical contact. In some embodiments, the position and orientation angle of the integrated device 160 can be adjusted independently.

The disadvantage to such a configuration is that both the device 160 and the structure 170 must now have either independent mounting systems within the vacuum chamber 120, or a well designed single stage for mounting that will allow the integrated device 160 to be inserted in close proximity to the photoemissive structure 170 and its independent support 470, and also allow its removal, without damaging or misaligning the photoemissive structure 170. The design of such mounting systems can be costly, especially when required to be used entirely within a vacuum chamber.

There are other design concerns for the joined stage 130, stage control 132, and connected stage 430 and its stage controls 432. If the photoemissive structure is to remain in a stable position relative to the electron optics, which is better for distortion control, then the design of the connected stage 430 holding the integrated device must be offset with enough distance from the photoemissive structure 170 so that changes in the relative orientation angle and position of the integrated device 160 relative to the beam of x-rays 411 could be made without the device coming in contact with the structure 170, disrupting the alignment with the electron optics.

In an alternative embodiment, the integrated device 160 could be mounted in close proximity to the photoemissive structure 170 and its independent support 470 and the motions of the stage 130 and the connected stage 430 rotated together if various orientation angles for the integrated device relative to the interior unmodified beam of x-rays 411 is desired. This may reduce the potential distortions caused by greater distance between device 160 and structure 170, but may increase the distortions caused by potential misalignments between the photoemissive structure 170 and the electron optics. Also, unless the photoemissive structure 170 were the same dimensions as the integrated device, a translation of the device 160 in x-y coordinates relative to the structure 170 may be required, so that the entire device can eventually be observed. To increase signal strength, a high x-ray flux is desired, and spreading the x-ray beam to cover the entire integrated device will reduce flux considerably.

Performance: Speed and Resolution

Given the descriptions above, the time to collect an image from a 1 cm×1 cm integrated device can be estimated, and compared to prior art Fresnel zone plate (FZP) systems such as those previously described.

The relative imaging throughput of this system can be estimated using three factors:

1. Flux of x-ray illumination
2. Contrast in the specimen under examination
3. Detection efficiency.

As noted above, the spectrum of the x-ray source used with the disclosed invention can be a broadband source, and in particular one in which a significant fraction of the x-rays have higher energy than the copper K-absorption edge. The source brightness can be as high as $5 \times 10^{10}$ x-ray photons/$mm^2$ srad, while the brightness in the FZP system is at least a factor of 10 smaller, since only the characteristic 8 keV copper Kα fluorescence photons are used.

Also, the numerical aperture (NA) of the system disclosed here can be approximately 9 mrad, while the NA of a FZP system is typically 3 mrad. The reduction in angle by a factor of 3 leads to a reduction in the amount of x-ray photons that can be collected and used to illuminate the specimen, reducing incident flux by a factor of 9.

These two differences alone lead to an increase in throughput by a factor of at least 90 due to the increased incident x-ray flux for the invention disclosed here.

The second factor affecting imaging speed (throughput) is image contrast. The imaging contrast (signal) depends on sample materials and x-ray energy (wavelength). As mentioned above, a FZP typically system uses 8 keV copper Kα fluorescence as its x-ray source, to which copper interconnects in an integrated device are mostly transparent (as was illustrated in FIG. 5). By using broadband light, with a significant portion with energy greater than the copper K-edge absorption at 8.9 keV, the contrast can increase by a factor of 15 or more. For an IC with a 50 micron thick silicon substrate, this corresponds to a 7× increase in signal contrast for a 1 micron thick copper line. The corresponding increase in throughput is a factor of $7^2$ or 49×.

The overall detector quantum efficiency (DQE) for the for the system according to the invention (factoring in the conversion from x-rays to an electron cascade in the photoemissive structure 170, the conversion of electrons to photons by the image converter 180, and then to electronic signals in the imaging system 190) is similar to that of existing FZP systems, about 2%. Therefore, the overall improvement in imaging speed is found by multiplying the increase in throughputs due to increased x-ray flux (90×) and image contrast (49×). This leads to an overall improvement in throughput for the disclosed system over the prior art FZP of 90×49=4,410.

Prior art FZP systems have been designed to inspect details of an integrated device, but not for high-resolution examination of entire ICs. To form a complete image of a 1 cm×1 cm IC using such a prior art system would take 200,000 hours (22.8 years). However, using the improvements of a system according to the invention disclosed here, data collection could occur 4,410 times faster, and a complete image could be collected in 45.3 hours—less than 2 days.

Of course, speed is not the only metric for such a microscope or inspection system. For integrated devices with 20 nm features, a resolution of 20 nm is desired. The resolution of a system according to the invention is partly determined by the diffusion of the cascade of electrons 177 in the photoemissive structure 170. This diffusion reduces the localization of the electron excitation, and causes a blur in the image.

This diffusion depends on the geometry and material composition of the photoemissive structure 170. A thicker structure will increase diffusion, creating more blur. Previous studies of x-ray-electron hybrid imaging systems [L. A. Bakaleynikov, E. Yu. Flegontova, and E. Zolotoyabko, "Combined X-ray-electron Imaging Techniques: Limitations on Lateral Resolution," Journal of Electron Spectroscopy and Related Phenomena, Vol. 151, pp. 97-104 (2005)] indicate that excitation of a photoemissive thin film of gold by an x-ray point-source can produce electron emission with a resolution as small as 20 nm. The electron optics can be designed such that they faithfully maintain this resolution without further degradation.

Further Extensions and Limitations

Although this disclosure presents an apparatus for the microscopic examination of integrated devices, and in particular copper integrated circuit structures, it will be recognized that the term "integrated devices" as used here can represent any manufactured object with small (e.g. micro- or nano-scale) features, such as silicon interposers with thru-silicon-vias (TSVs), packages containing multiple integrated circuits (3D-IC structures), especially those with TSVs to connect them vertically, MEMS and NEMS devices such as micro-actuators and micro-sensors, RF antenna structures, integrated optical devices, multi-function IC packages for cellular phones, photomasks, metamaterials, magnetic storage devices, and others that will be known to those skilled in the art.

It will also be recognized that the apparatus disclosed here can be used for the examination of objects other than manufactured integrated structures. Such objects can include mineral formations or biological tissue samples, especially biological tissue samples that may have been metallized for enhanced contrast. As long as the wavelength range for the beam of x-rays is selected such that there is measurable contrast in the absorption or scattering of x-rays from the internal structures of the object under investigation, a system as disclosed here can be used to investigate these internal structures as well.

It will also be recognized that this microscope can be used as a component of an inspection system, in which the representations of the 2-D and 3-D structures are compared with stored reference data. These data can be either a reference image or set of images from a similar device known to have been properly manufactured (a "Golden Image"), or data from a similar region in the integrated device previously that has been measured, or from a database representing the integrated device design rules or geometric structures as designed.

With this application, several embodiments of the invention, including the best modes for various circumstances, have been disclosed. It will be recognized that, while specific embodiments may be presented, elements discussed in detail only for some embodiments may also be applied to others. For example, the image collection discussed in detail only for the first embodiment can be applied to other embodiments as well. Likewise, the angular variation of the x-rays described in detail in the third embodiment may find application in other configurations.

While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

I claim:

1. An apparatus for the examination of an integrated device, comprising:
    a source of x-rays;
    a vacuum chamber;
    a stage for holding an integrated device, positioned outside the vacuum chamber;
    a window that allows the transmission of x-rays into the vacuum chamber;
    a photoemissive structure within the vacuum chamber designed to emit electrons when exposed to x-rays;
    an electron optical system within the vacuum chamber, designed to form a magnified image of electrons emitted from the photoemissive structure; and
    a means of adjusting the position and orientation angle of the stage holding the integrated device relative to the x-rays.

2. The apparatus of claim 1, in which
    the photoemissive structure comprises material containing gold, and
    the photoemissive structure comprises material containing cesium iodide (CsI).

3. The apparatus of claim 1, in which
    the photoemissive structure comprises a layer of gold having a thickness between 5 nm and 100 nm; and
    the photoemissive structure comprises a layer of cesium iodide (CsI) having a thickness between 3 nm and 200 nm.

4. An apparatus for the examination of an integrated device, comprising:
    a source of x-rays;
    a vacuum chamber;
    a stage for holding an integrated device, positioned outside the vacuum chamber;
    a window that allows the transmission of x-rays into the vacuum chamber;
    a photoemissive structure within the vacuum chamber designed to emit electrons when exposed to x-rays; and
    an electron optical system within the vacuum chamber, designed to form a magnified image of electrons emitted from the photoemissive structure; and
    a means of adjusting the position and orientation angle of the x-rays relative to the stage holding the integrated device.

5. The apparatus of claim 4, in which
    the photoemissive structure comprises material containing gold, and
    the photoemissive structure comprises material containing cesium iodide (CsI).

6. The apparatus of claim 4, in which
    the photoemissive structure comprises a layer of gold having a thickness between 5 nm and 100 nm; and
    the photoemissive structure comprises a layer of cesium iodide (CsI) having a thickness between 3 nm and 200 nm.

7. An apparatus for the examination of an integrated device, comprising:
    a vacuum chamber;
    a stage for holding an integrated device, positioned outside the vacuum chamber;
    a window that allows the transmission of x-rays into the vacuum chamber;
    a photoemissive structure within the vacuum chamber designed to emit electrons when exposed to x-rays; and
    an electron optical system within the vacuum chamber, designed to form a magnified image of electrons emitted from the photoemissive structure; and
    a means of adjusting the position and orientation angle of the photoemissive structure.

8. An apparatus for the examination of an integrated device, comprising:
    a vacuum chamber;
    a stage for holding an integrated device, positioned outside the vacuum chamber;
    a window that allows the transmission of x-rays into the vacuum chamber;
    a photoemissive structure within the vacuum chamber designed to emit electrons when exposed to x-rays; and
    an electron optical system within the vacuum chamber, designed to form a magnified image of electrons emitted from the photoemissive structure; and
    an image converter that absorbs incident electrons and emits photons; and
    an image collector to produce images of the emitted photons.

9. The apparatus of claim 8, additionally comprising:
    a window that allows the transmission of the emitted photons out of the vacuum chamber; and in which
    the image collector to produce images of the emitted photons is outside the vacuum chamber.

10. The apparatus of claim 8, additionally comprising:
    a means of converting the images of the emitted photons into electronic signals.

11. The apparatus of claim 10, additionally comprising:
    a means of recording the electronic signals.

12. The apparatus of claim 11, additionally comprising:
    a system controller that directs:
    the motion of the stage holding the integrated device and
    the means of recording of the electronic signals corresponding to the images.

13. An apparatus for the examination of an integrated device, comprising:
    a vacuum chamber;
    a window that allows the transmission of x-rays into the vacuum chamber;
    a stage for holding an integrated device, positioned inside the vacuum chamber;
    a photoemissive structure within the vacuum chamber designed to emit electrons when exposed to x-rays; and
    an electron optical system within the vacuum chamber, designed to form
    a magnified image of electrons emitted from the photoemissive structure.

14. The apparatus of claim 13, additionally comprising:
    a source of x-rays.

15. The apparatus of claim 14, additionally comprising:
    a means of directing the x-rays from the source of x-rays onto an integrated device held on the stage.

16. The apparatus of claim 14, additionally comprising:
    a means of adjusting the position and orientation angle of the stage holding the integrated device relative to the x-rays.

17. The apparatus of claim 14, additionally comprising:
    a means of adjusting the position and orientation angle of the x-rays relative to the stage holding the integrated device.

18. The apparatus of claim 13, in which
the photoemissive structure comprises material containing gold.
19. The apparatus of claim 13, in which
the photoemissive structure comprises a layer of gold.
20. The apparatus of claim 19 in which
the thickness of the gold layer is between 5 nm and 100 nm.
21. The apparatus of claim 13, in which
the photoemissive structure comprises material containing cesium iodide (CsI).
22. The apparatus of claim 13, in which
the photoemissive structure comprises a layer of cesium iodide (CsI).
23. The apparatus of claim 22, in which
the thickness of the CsI layer is between 3 nm and 200 nm.
24. The apparatus of claim 13, additionally comprising:
a means of adjusting the position and orientation angle of the photoemissive structure.
25. The apparatus of claim 13, additionally comprising:
an image converter that absorbs incident electrons and emits photons; and
an image collector to produce images of the emitted photons.
26. The apparatus of claim 25, additionally comprising:
a window that allows the transmission of the emitted photons out of the vacuum chamber; and in which
the image collector to produce images of the emitted photons is outside the vacuum chamber.
27. The apparatus of claim 25, additionally comprising:
a means of converting the images of the emitted photons into electronic signals.
28. The apparatus of claim 27, additionally comprising:
a means of recording the electronic signals.
29. The apparatus of claim 28, additionally comprising:
a system controller that directs:
the motion of the stage holding the integrated device, and
the means of recording of the electronic signals corresponding to the images.
30. The apparatus of claim 13, in which
the integrated device is an integrated circuit.
31. The apparatus of claim 13, in which
the integrated device is a silicon interposer with through-silicon vias.
32. The apparatus of claim 13, in which
the stage that holds the integrated device also holds the photoemissive structure.
33. The apparatus of claim 32, in which
the stage that holds the integrated device and the photoemissive structure has been designed so that the integrated device can be inserted and removed.
34. The apparatus of claim 33, in which
means is provided to adjust the position and orientation angle of the integrated device relative to the photoemissive structure.
35. The apparatus of claim 33, in which
the stage that holds the integrated device and the photoemissive structure has been designed so that the integrated device can be inserted and positioned in close proximity to the photoemissive structure.
36. The apparatus of claim 13, in which
the stage that holds the integrated device also holds the photoemissive structure, and
the photoemissive structure has been manufactured directly on the integrated device to be examined.
37. A system for the inspection of an integrated device, comprising:
a source of x-rays;
a stage for holding an integrated device;
a photoemissive structure that absorbs x-rays and emits electrons;
a system of electron optics that forms a magnified image of the photoemissive structure;
a means of converting the magnified image into an electronic signal;
a means for comparing the electronic signal to stored reference data; and
a means of adjusting the position and orientation angle of the x-rays relative to the stage holding the integrated device.
38. The system of claim 37, additionally comprising:
a means for adjusting the position and orientation angle of a source of x-rays relative to the stage holding the integrated device; and
a system controller that directs:
the means of adjusting the position and orientation angle of the source of x-rays,
the motion of the stage holding the integrated device, and
the means of storing of the electronic signals corresponding to the images.

* * * * *